(12) United States Patent
Wang

(10) Patent No.: US 10,190,156 B2
(45) Date of Patent: Jan. 29, 2019

(54) METHODS AND SYSTEMS FOR USING BUILT-IN STANDARD CURVE TO MEASURE MOLECULAR NUMBERS OF BIOLOGICAL COMPONENTS

(71) Applicant: Zheng Wang, Bethesda, MD (US)

(72) Inventor: Zheng Wang, Bethesda, MD (US)

(73) Assignee: W2 Biosolutions, LLC, Bethesda, MD (US)

( * ) Notice: Subject to any disclaimer, the term of this patent is extended or adjusted under 35 U.S.C. 154(b) by 838 days.

(21) Appl. No.: 14/251,802

(22) Filed: Apr. 14, 2014

(65) Prior Publication Data

US 2015/0080240 A1 Mar. 19, 2015

Related U.S. Application Data

(60) Provisional application No. 61/750,018, filed on Apr. 15, 2013.

(51) Int. Cl.
*C12Q 1/68* (2018.01)
*C12Q 1/6837* (2018.01)

(52) U.S. Cl.
CPC ................................. *C12Q 1/6837* (2013.01)

(58) Field of Classification Search
None
See application file for complete search history.

(56) References Cited

U.S. PATENT DOCUMENTS

2006/0115840 A1* 6/2006 Boucher et al. ..... C12Q 1/6837
435/6.11

OTHER PUBLICATIONS

Bissels et al., "Absolute quantification of microRNAs by using a universal reference," RNA 2009, 15:2375-2384.*
Heller, "DNA Microarray Technology: Devices, Systems, and Applications," Annu. Rev. Biomed. Eng. 2002, 4:129-153.*
Yauk et al., "Novel design and controls for focused DNA microarrays: applications in quality assurance/control and nomialization for the Health Canada ToxArray," BMC Genomics 2006, 7:266.*
Pachter 2014: "Estimating number of transcripts from RNA-Seq measurements, Bits of DNA: Reviews and Commentary on Computational Biology" (liorpachter.wordpress.com).
Armstrong 2014 : "6 Changes That'll Make a Big Difference With Your RNA-seq, Cofactor Genomics" (cofactorgenomics.com).
Bissels et al., Absolute quantification of microRNAs by using a universal reference, RNA, 2009, pp. 2375-2384, vol. 15.
Yauk et al., Novel design and controls for focused DNA microarrays: applications in quality assurance . . . for the Health Canada ToxArray, BMC Genomics, 2006, pp. 266, vol. 7.

* cited by examiner

*Primary Examiner* — Kaijiang Zhang
(74) *Attorney, Agent, or Firm* — Syncoda, LLC; Junjie Feng

(57) ABSTRACT

Methods and devices are disclosed, which perform absolute quantification assay of functional components of biological specimens. The present application relates to manufacture built-in standard curve(s) and computational analysis. The present application further relates to methods for the measurements of such biological components, for example, biochips, PCR arrays, microarrays, and ELISA array.

13 Claims, 12 Drawing Sheets

METHODS AND SYSTEMS FOR USING BUILT-IN STANDARD CURVE TO MEASURE MOLECULAR NUMBERS OF BIOLOGICAL COMPONENTS

BACKGROUND

I. Field of the Invention

The present invention relates to device and computational analysis to perform absolute quantification assay to measure the molecular copy numbers of the functional components of biological specimens in biosensor detection systems.

II. Description of Related Art

The success of the Human Genome Project has paved the solid foundation for understanding each gene's function. However, we are facing the next challenge on the study of functional genomics as we are lack of powerful and reliable expression analysis and methods to assess the epigenome (COLLINS 2010). In gene expression studies, many methods have been developed to perform assays, such as RT-PCR (JURADO et al. 2003, MIURA et al. 2008, STRISSEL et al. 2012), DNA microarray (SCHENA et al. 1995, HANNAH et al. 2008, MALONE et al. 2011) and sequencing (SHENDURE et al. 2008, FULLER et al. 2009, METZKER 2009) for RNA level expression analysis; western blot (MAHMOOD et al. 2012), ELISA (LEQUIN 2005), and protein microarray (TEMPLIN et al. 2002, CRETICH et al. 2014) for protein level expression analysis. But all of them cannot meet the need of expression analysis of functional genomics studies (TAO et al. 1999, CARNEY et al. 2012, RENAUD et al. 2014).

The fundamental obstacle of transcriptome profile analysis rises from the fact that most experimental expressional data are relative quantification data (for example, disease vs. normal), not absolute quantification data (RENAUD et al. 2014, BALL et al. 2002, GERSHON 2002, QUACKENBUSH 2003, BAMMLER et al. 2005, ALLISON et al. 2006, JONES et al. 2007, IOANNIDIS 2009). This is a severe bottleneck in Big Data To Knowledge (BD2K), thus, the current project of National Institutes of Health's BD2K calls for standardizing data/metadata and integrating biomedical data (National Institutes of Health (NIH): Big Data to Knowledge). Therefore, a true absolute quantification method of expression profile is urgently needed.

SUMMARY

The present application relates to a method of determining the absolute quantity of a molecule of interest (sample target), comprising:
i. providing a first molecule as control partner 1 and a second molecule as sample probe;
ii. providing a third molecule as control partner 2 and a fourth molecule as sample target;
iii. providing a series of control partner 1 with different and known copy numbers;
iv. attaching the series of control partner 1 onto a solid support at separate locations;
v. attaching at least one sample probe or at least one sample target onto the solid support;
vi. contacting at least one control partner 2 with the series of control partner 1, wherein the series of control partner 1 recognize and bind the at least one control partner 2, resulting directly or indirectly in a series of detectable control signals, wherein the intensity of each location of the detectable control signals correlates with the known copy number of the control partner 1 in the series of control partner 1, wherein the copy number of control partner 2 is no less than the copy number of control partner 1;
vii. detecting the control signals and making a standard curve relating the signal intensities of the series of detectable control signals with the known copy number of the control partner 1 in the series of control partner 1;
viii. adding at least one sample target or at least one sample probe to allow the at least one sample probe contacting with the at least one sample target, wherein the at least one sample probe recognizes and binds the at least one sample target, resulting directly or indirectly in a detectable sample signal, wherein the intensity of each location of the detectable sample signals correlates with the copy number of the at least one sample target, wherein the copy number of sample probes is no less than the copy number of sample targets;
ix. determining the copy number of the at least one sample target by using the standard curve to translate the sample signal intensity to the copy number of the at least one sample target.

In one embodiment, the control partner 2 is directly or indirectly labeled with one or more basic labeling units, wherein the at least one sample target or the at least one sample probe are directly or indirectly labeled with basic labeling units, wherein the detectable signals are the signals from the basic labeling units directly or indirectly on the control partner 2 and the basic labeling units directly or indirectly on the at least one sample target or the at least one sample probe. In another embodiment, the signals are detected at the locations to which the control partner 1, the at least one sample probe or the at least one sample target are attached, wherein the control partner 2, the at least one sample probe or the at least one sample target are labeled with one or more basic labeling units, wherein the signal intensities of the labeled control partner 2, the at least one sample probe or the at least one sample target are transformed into signal intensity unit (IU) or sum of IU (SIU), wherein SIU is obtained by dividing the signal intensity at a location on the solid support by the number of basic labeling units per molecule that is labeled with basic labeling unit, wherein IU is obtained by dividing the SIU by the copy number of the molecules directly or indirectly labeled with basic labeling units at the location, wherein the copy number of the directly or indirectly labeled control partner 2 is the copy number of control partner 2 that are bound to control partner 1.

In yet another embodiment, the standard curve in step vii is made with regression analysis.

In yet another embodiment, the at least one sample probe binds the at least one sample target and the control partner 1 bind the control partner 2 at approximately constant ratio.

In yet another embodiment, the at least one sample probe binds the at least one sample target and the control partner 1 bind the control partner 2 at approximately one molecule to one molecule ratio.

In yet another embodiment, the provided molecules in step i and ii are selected from the group consisting of: (i) DNA, (ii) RNA, (iii) protein, (iv) peptide, (v) polysaccharide, (vi) chemical compound and (vii) antibody.

In yet another embodiment, the solid support is selected from a group consisting of: (i) glass, (ii) plastic, (iii) silicon, (iv) microscopic polystyrene beads, (v) nitrocellulose membrane, (vi) PVDF, (vii) metal, and (viii) multiple-well plate.

In yet another embodiment, the at least one sample probe or the at least one sample target and control partner 1 are premade prior to being attached as spots of serial dilutions of known value to the solid surface.

In yet another embodiment, the control partner 1 and the at least one sample probe or the at least one sample target are directly synthesized on the solid support.

In yet another embodiment, the "synthesized" is carried out with photolithographic synthesis.

In yet another embodiment, the control partner 2 and the at least one sample target or the at least one sample probe are directly or indirectly labeled by a labeling method by applying from the group consisting of: (i) fluorophore, (ii) chemiluminescent agent, (iii) silver, (iv) affinity, (v) photochemical agent, (vi) enzyme, (vii) chromophore, and (viii) radioisotope tags.

In yet another embodiment, the signal intensity is detected with a microarray laser scanner.

In yet another embodiment, the signals are detected by label-free technology. In yet another embodiment, the label-free technology is surface plasmon resonance (SPR), microelectromechanical system (MEMS), carbon nanowire sensors or carbon nanotubes.

Another aspect of the present application relates to a method of determining the absolute quantity of a molecule of interest, comprising:
  i. providing a first molecule as control partner 1 and a second molecule as sample probe;
  ii. providing a third molecule as control partner 2 and a fourth molecule as sample target;
  iii. attaching a series of control partner 1 with different and known copy numbers onto separate wells on a multiple-well plate;
  iv. attaching at least one sample probe or at least one sample target onto a well not occupied by control partner 1 on the plate;
  v. contacting at least one control partner 2 with the series of control partner 1 in separate wells, wherein the series of control partner 1 recognize and bind the at least one control partner 2, resulting in a series of complex of control partner 1 and control partner 2 with the known copy number of the control partner 1 in the series of control partner 1, wherein the copy number of control partner 2 is no less than the copy number of control partner 1, wherein the control partner 2 is directly or indirectly labeled with basic labeling unit;
  vi. adding at least one sample target or at least one sample probe into a well to allow the at least one sample probe contacting with the at least one sample target, wherein the at least one sample probe recognizes and binds the at least one sample target, resulting in a complex of sample target and sample probe, wherein the copy number of sample probes is no less than the copy number of sample targets, wherein the sample target or sample probe is directly or indirectly labeled with basic labeling unit;
  vii. adding a substrate into the wells to produce a color by the labels on the complexes, wherein the color intensity of each well correlates with the copy number of the control partner 1 or with the copy number of the sample target;
  viii. detecting the intensity of the color signals by a plate reader;
  ix. making a standard curve relating the signal intensities of the complexes of control partner 2 and series of control partner 1 with the known copy numbers of the control partner 1 in the series of control partner 1, wherein the standard curve is made with regression analysis;
  x. determining the copy number of the sample target in the well by using the standard curve to translate the sample signal intensity to the copy number of the sample target.

In one embodiment, the basic labeling unit is an enzyme, wherein the enzyme directly labels the control partner 2 and sample target or sample probe, respectively, wherein the enzyme reacts with the substrate to produce the color. In another embodiment, the control partner 2 and sample target or sample probe are indirectly labeled via a "bridge" that can unite the molecule of interest and a molecule carrying an enzyme, wherein the enzyme reacts with the substrate to produce the color.

Another aspect of the present application relates to a method of determining the absolute quantity of a molecule of interest, comprising:
  i. providing a first molecule as control template and a second molecule (molecule of interest) as sample template;
  ii. depositing a series of control templates with different and known copy numbers into separate wells on a multiple-well plate;
  iii. depositing at least one sample template into a well not occupied by a control template on the plate;
  iv. amplifying the series of control templates and the at least one sample template by PCR (polymerase chain reaction) with a pair of primers that complements the control template and a pair of primers that complements the at least one sample template, respectively, wherein the amounts of PCR products in copy numbers from series of control templates reflect the known copy numbers of control templates before the PCR reactions, wherein the amount of PCR product in copy number from the at least one sample template reflects the copy number of the at least one sample template before the PCR reaction;
  v. detecting the PCR products with a binding partner that specifically binds the PCR products, wherein the binding partner has one or more basic labeling unit, wherein the basic labeling unit emits a detectable signal;
  vi. transforming the signal intensity of the detectable signal into intensity unit (IU) or sum of IU (SIU), wherein SIU is obtained by dividing the signal intensity in a well by the number of basic labeling units per PCR product molecule that binds with binding partner that has the basic labeling unit, wherein IU is obtained by dividing the SIU by the copy number of the sample or control template before PCR amplification;
  vii. making a standard curve relating the signal intensities of the series of control templates with the known copy numbers of the control templates in the series of control templates for each PCR cycle in the exponential phase, wherein the standard curve is made with regression analysis;
  viii. determining the copy number of the sample template before PCR reaction by using the standard curve to translate the sample signal intensity to the copy number of the sample template.

In one embodiment, the binding partner in step v is an oligonucleotide that specifically binds the PCR products.

In another embodiment, the oligonucleotide is a dual-labeled probe, wherein the dual-labels consist of a fluorophore attached to the 5'-end of the probe and a quencher at the 3'-end.

In yet another embodiment, the binding partner in step v is a dsDNA (double strand DNA) dye that specifically binds the double-stranded PCR products.

In yet another embodiment, the dye is a dye selected from the group consisting of: (i) SYBR Green I, (ii) PicoGreen, (iii) QuantiFluor, (iv) AccuBlue, (v) Hoechst 33258, (vi) BEBO, and (vii) AccuClear.

In yet another embodiment, in step viii the standard curve and sample signal intensity are from the same PCR cycle.

INCORPORATION BY REFERENCE

All references in this specification are herein incorporated by reference to the same extent as if each individual publication was specifically and individually indicated to be incorporated by reference.

Further features and advantages of certain embodiments of the present application will become more fully apparent in the following description of the embodiments and drawings thereof, and from the claims.

BRIEF DESCRIPTION OF THE DRAWINGS

The foregoing and other features and advantages of the present application will be more fully understood from the following detailed description of illustrative embodiments taken in conjunction with the accompanying drawings in which:

FIG. 14 provides a diagram to illustrate what the computer software is composed of.

DETAIL DESCRIPTION OF VARIOUS EMBODIMENTS

Figure 1:
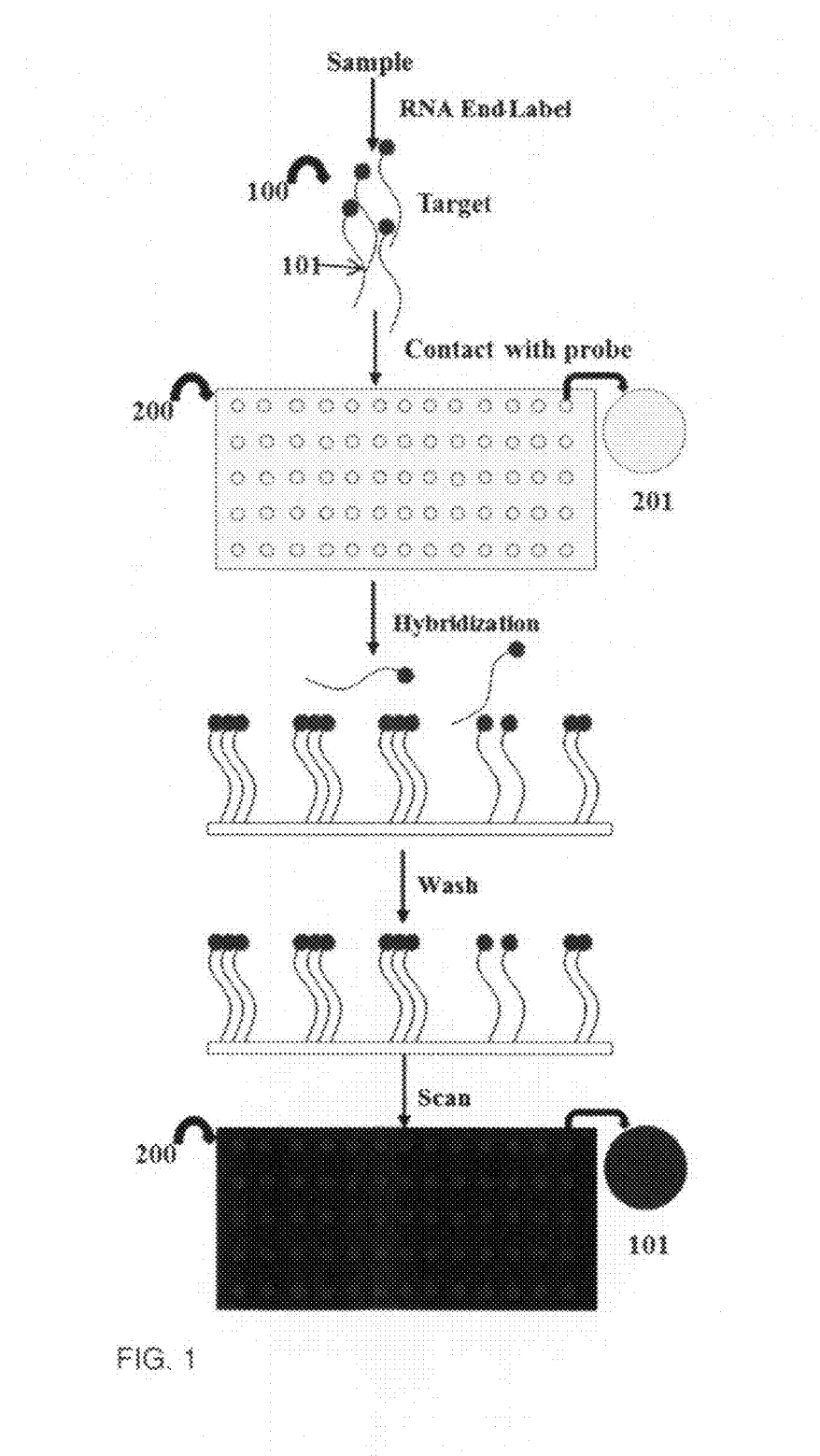
FIG. 1 provides a schematic representation of gene expression microarray technology.

For decades, scientists have been trying to measure the absolute levels of gene expression; however, it has not been successful. The basic concept of this invention is to develop experimental techniques which are capable of measuring absolute levels of key components of biological molecules, such as miRNA, mRNAs, DNA strands, proteins, peptides, polymers, polysaccharide, phospholipid, metabolite, and chemical compound. Thus, the measured biological data can meet the requirements of standardization and integration in functional genomics studies.

The polymerase chain reaction (PCR) is a widely used biomedical technology which can quantitatively determine levels of gene expression and is often called the gold standard in gene quantitative field. However, most quantitatively analyzed PCR data are relative data. Although the emerging technique of digital PCR (dPCR) (WARREN et al. 2006, FU et al. 2014) offers a unique approach to measure the copies of specific nucleic acids, dPCR is prone to saturation and inevitably fails when all reactions are positive; has disagreement comparing the estimated DNA copies with the result of UV spectrophotometry measurement. Mostly, dPCR is neither cost efficient nor high-throughput because it only assay one or two gene(s) each time (MOJTAHEDI et al. 2014, SANDERS et al. 2011). Thus, PCR/dPCR cannot meet the need of expression analysis of functional genomics studies.

Sequencing technologies have been used in facilitating gene expression analysis, too. The early developed methods are tag based serial analysis of gene expression (SAGE) (ADAMS et al. 1991, VELCULESCU et al. 1995) and massively parallel signature sequencing (MPSS) (REINARTZ et al. 2002, BRENNER et al. 2000, TORRES et al. 2008). The recent next generation sequencing technologies allow RNA-seq being feasible (SHENDURE et al. 2008, FULLER et al. 2009, METZKER 2009). But RNA-seq has biases associated with transcript lengths, lacks uniform coverage of regions in mRNA, Tag-seq methods either have biases or not high-throughput, and yet the newly reported EXPRSS Tag-seq method cannot perform absolute quantification of expression profiling (RALLAPALLI et al. 2014) either. The fundamental principle of RNA-seq is that the expression level of each RNA unit is measured by the number of sequenced fragments that map to the transcript (RPKM: Reads Per Kilobase per Million mapped reads), which is expected to correlate directly with its abundance level (MORTAZAVI et al. 2008). Although RPKM is called absolute gene expression data and used in transcriptomic database construction (LEE et al. 2012, XU et al. 2014), it by no mean reflects gene copy number. Since the precise quantification of mRNA abundance is critical, various statistical methods have been proposed to model the variance among samples in biological groups, aimed to improve overall fitting of RNA-seq count data (MUNGER et al. 2014, GU et al. 2014, RAPAPORT et al. 2013). Moreover, the Encyclopedia of DNA Elements (ENCODE) Consortium (National Human Genome Research Institute (NHGRI): the Encyclopedia of DNA Elements (ENCODE) Consortium), an international collaboration of research groups funded by the National Human Genome Research Institute (NHGRI), has been also working to determine the copy numbers of transcripts based on RPKM/FPKM information since 2003 with little success (KELLIS et al. 2014, DJEBALI et al. 2012, PACHTER 2014). Until Apr. 30, 2014, the best work "on the connection between transcript copy numbers and RNA-Seq measurements is the careful work of Marinov et al. in 'From single-cell to cell-pool transcriptomes: stochasticity in gene expression and RNA splicing'" (MARINOV et al. 2014), commented by Lior Pachter (PACHTER 2014). That work was accomplished by utilizing spike-in method (described in more detail in microarray section). However, that work "is far from ideal, as it depends on the accuracy of quantification of the spike-ins and assumes the absence of systemic differences between spike-in RNAs and endogenous RNAs. If these assumptions are wrong, a systematic error is expected in the calculated number of mRNAs per cell" (MARINOV et al. 2014) and sure enough those assumptions are not one hundred percent right (PACHTER 2014, ARMSTRONG 2014). Thus, sequence technology has not found the solution to determine gene copy number.

Microarray is the first rapid and high-throughput technology in the quantification of gene expression (SCHENA et al. 1995) which is one of the most powerful and widely used tools in revealing gene expression profiles (GIT et al. 2010, CHAN et al. 2009, ARBEITMAN et al. 2002, SPELLMAN et al. 1998, ALIZADEH et al. 2000, GOLUB et al. 1999, BREM et al. 2002, ZHANG et al. 2007, SHI et al. 2010, ADABOR et al. 2014, KORUCUOGLU et al. 2014), but microarray has been facing the similar fundamental challenge: data standardization is not possible because of the fact that expressional microarray data is relative quantification data, instead of absolute quantification data (BALL et al. 2002, GERSHON 2002, QUACKENBUSH 2003, BAMMLER et al. 2005, ALLISON et al. 2006, JONES et al. 2007, IOANNIDIS 2009). The fundamental principle of expression microarray is that the expression level of each RNA unit is measured by the signal intensity via an affinity-based biosensor platform. In the very first published microarray paper, Schena et al. used color-1 and color-2 to label sample-1 and sample-2, respectively; and added an equal amount of foreign mRNA to sample-1 and sample-2 before labeling. To assay the alteration in gene expression patterns of those two samples, they normalized the sample signal by matching the signals resulting from the added foreign mRNA, and compared the normalized signal intensities between two samples to obtain gene expression fold changes (SCHENA et al. 1995). The two-color hybridization method cancels the difference caused by target features and the sequence of the gene (EISEN et al. 1999, EISEN et al. 1998). Thus, it maximizes the reliability and precision to quantitate relative differences in the abundance of two RNA samples, and is widely used (ROSS et al. 2000, CHANG et al. 2002, PEROU et al. 2000, GARBER et al. 2001, CHEN et al. 2002, WHITFIELD et al. 2002, PUSKAS et al. 2002, STERRENBURG et al. 2002, WEIL et al. 2002, NOVORADOVSKAYA et al. 2000). Those differential microarray co-hybridization assays measure the relative gene expression of paired query and reference samples, but the real power of microarray analysis comes from identification of informative patterns of gene expression across multiple experiments. Compared to the two-color platform, Affymetrix developed a one-color platform with optional spiking known concentrations of foreign transcripts at various concentrations (LOCKHART et al. 1996). The spike-in is used in the normalization process for differences between separate arrays to allow consistent comparisons on relative expression levels; and it was further developed to estimate the minimum detectable frequency on the array, the 'array sensitivity' value, which is useful as a quality-control metric for individual hybridizations and is also used to adjust signals from low-level transcripts (LOCKHART et al. 1996, SARTOR et al. 2006, ZHOU et al. 2012, HILL et al. 2001, CHOE et al. 2005, COPE et al. 2004, WELSH et al. 2013). Affymetrix platform extracts the "absolute expression value" for each transcript with or without normalized to spike-in references. Thus, results can be directly compared to data for any other target using the same probe set. Since then, many complex mathematical algorithms have been introduced into microarray data analysis including linear models (WOFINGER et al. 2001, CHU et al. 2002, YANG et al. 2003) and empirical bayes (FRIEDMAN et al. 2000, BALDI et al. 2001, LONG et al. 2001, TOWNSEND et al. 2002). All of them have been focused on using computational methods to ensure that true variances can be detected for differentially expressed genes across specified conditions in designed microarray experiments because identifying those genes is a massive multiple testing problem in which one or more tests are conducted for each of tens of thousands of genes (WOFINGER et al. 2001, CHU et al. 2002, YANG et al. 2003, FRIEDMAN et al. 2000, BALDI et al. 2001, LONG et al. 2001, TOWNSEND et al. 2002, SMYTH 2004). The "absolute expression value" measured by one-color platform and used in mathematic models indicates the individual signal intensity of microarray spot, instead of the biological meaning of gene copy number (SARTOR et al. 2006, NEWTON et al. 2001, LIANG et al. 2004, SEITA et al. 2012). Thus, different experimental microarray approaches have been tested to assay the true expression levels which can be compared in any experiments.

Frigessi et al. developed a TransCount method based on Bayesian statistical modeling, which can be used to calculate the concentration from the signal intensity of each probe on spotted arrays and the concentration estimate seems to be a more reliable measure of the transcript abundance than the usually used expression ratio (FRIGESSI et al. 2005). The same had continued to develop the TransCount method to estimate the absolute transcript concentrations by using a reference (NYGAARD et al. 2005, NYGAARD et al. 2008). However, in determining experiment absolute concentration levels, Held et al. found that statistical model is not as favorable as spike-in method (HELD et al. 2006) and the TransCount method has not been adopted by others in the field. Although it is well known that the normalization step of microarray data is crucial in downstream expression analysis, normalization methods including spike-in fail because all of them rely on certain assumptions to make relative normalization (LOCKHART et al. 1996, SARTOR et al. 2006, ZHOU et al. 2012, HILL et al. 2001, CHOE et al. 2005, COPE et al. 2004, WELSH et al. 2013, CALZA et al. 2008). The extreme difficulty to quantify microarray signal data is caused by a complex relationship between the amount of input RNA for a given gene and the intensity of the probe signal at a corresponding hybridization target. This relationship depends on a multitude of factors, including the labeling method, hybridization conditions, target features and the sequence of the gene. Therefore, microarray based methods are generally used to assay the relative representation of RNA (for example, disease vs. normal) (SCHENA et al. 1995, LOCKHART et al. 1996, SARTOR et al. 2006, ZHOU et al. 2012, HILL et al. 2001, CHOE et al. 2005, COPE et al. 2004, WELSH et al. 2013, HELD et al. 2006, CALZA et al. 2008, NISHIYAMA et al. 2013, HIRATA et al. 2012). Yang et al. used a common reference sample that provided a baseline expression measure for each gene, enabling normalization and comparison of independent experiments (YANG et al. 2002) and this approach was further developed as universal reference (UR) RNA (NOVORADOVSKAYA et al. 2004, BISSELS et al. 2009). However, this method costs twice and it is not feasible to establish a true universal reference either. Constant efforts have been made to standardize microarray data, such as the MicroArray Quality Control (MAQC) consortium's MAQC-II project, a project designed to evaluate the sources of bias in each individual study, with goals to understand sources of variability in prediction performance and to assess the influences of endpoint signal strength in data (SHI et al. 2010). However, gold standard remains elusive.

More than a decade ago, Dudley et al. pointed out that the idea microarray data is copy numbers which permit comparison between different experiments, laboratories, experimental systems, and data types, a crucial aspect of the data base dependent analysis of biological systems that the field of functional genomics requires (DUDLEY et al. 2002). Their approach was similar as Yang's, involved in using labeled common oligo reference and two-color hybridization. Ratios between sample intensities and intensities of the oligo reference measure sample RNA levels on a scale that relates to their absolute abundance, instead of to the variable and unknown abundances. Again, it provides an absolute expression measurement, but not as copy numbers yet. Carter et al. pioneered a method to experimentally measure copy number using spike-in exogenous RNA controls and two-color hybridization (CARTER et al. 2005). However, this method is neither easy in handling, nor precise in measuring; and is not adopted by others, nor used by the same group in their later experiments (NISHIYAMA et al. 2013, HIRATA et al. 2012). Bissels et al employed UR with known amount and two-color hybridization to measure RNA copy number (BISSELS et al. 2009). However, the UR does not cancel the bias related to labeling and it has twice the cost and labor requirements. Thus, there is no established method which can measure gene copy number by microarray.

Therefore, a real breakthrough in gene expression copy number assay is urgently needed, especially at high-throughput scale, at today's Big Data To Knowledge (BD2K) era (National Institutes of Health (NIH): Big Data to Knowledge). This innovation is aimed to offer a simple, yet effective approach to innovate the conventional relative gene expression measurements to be able to perform absolute gene copy number quantification that ties in with two major challenges (standardizing data/metadata and integrating biomedical data) which are on the list of the current mission of National Institutes of Health's BD2K (National Institutes of Health (NIH): Big Data to Knowledge). The approach of the present invention is applicable in different platforms of biosensor detection systems to contribute maximally to the need of standardization and integration of biological data.

Biosensor detection systems typically consist of biorecognition component, biotransducer component, and biosensor reader device. The system takes advantage of the selective interaction and binding (affinity) of certain biological molecules to identify molecular structures and furthermore measure levels of different analytes (i.e. the specific substance whose presence is being quantitatively or qualitatively analyzed) (TURNER 1987, BĂNICĂ 2012, SIN et al. 2014, ESTEVEZ et al. 2014). Affinity-based biosensors exploit selective binding and interaction of certain bio-molecules (recognition probes) to detect specific target analytes in biological samples. The following are some examples of biosensor detect platforms. Membrane-based antibody arrays are based on the sandwich immunoassay principle. A panel of antibodies (probe, function as capture) is immobilized in specific spot locations on the surface of membrane to capture proteins (target) by corresponding antibodies. ELISA arrays are based on the same principle of membrane-based antibody arrays; however, antibodies are immobilized in specific wells of multiple-well plates. Microarrays are densely packed biosensor arrays which detect thousands of different analytes simultaneously are popular in genomics, proteomics, molecular diagnostics, and systems biology. PCR also belongs to the biosensor platforms with amplification involved in the measured particular DNA sequence. The essential role of biosensor platforms is to exploit specific bindings of the probe-target complexes to produce detectable signals, which correlate with the presence of the targets and conceivably their abundance. Detection methods can be label or label-free technologies.

Reference will now be made in detail to some embodiments, examples of which are illustrated in the accompanying drawings. Wherever possible, the same reference numbers are used throughout the drawings to refer to the same or like parts.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

It must be noted that as used in this specification and the appended claims, the singular forms "a," "an," and "the" include plural reference unless the context clearly dictates otherwise. Unless defined otherwise all technical and scientific terms used herein have the same meaning as commonly understood to one of ordinary skill in the art to which this invention belongs.

I. Microarrays

A microarray is a multiplex lab-on-a-chip. It is a 2D array on a solid substrate (usually a glass slide, nitrocellulose membrane, bead, multiple-well plate, or silicon thin-film cell) that assays large amounts of biological material using high-throughput screening miniaturized, multiplexed and parallel processing and detection methods. The microarray can be DNA microarray, protein microarray, peptide microarray, tissue microarray, cellular microarray, chemical compound microarray. The miRNA microarray provides the profile of miRNA expression; the peptide microarray provides detailed analyses or optimization of protein-protein interactions; tissue microarray provides multiplex histological analysis; the cellular microarray provides the multiplex interrogation of living cells on the surface of a solid support; the chemical compound microarray which is a collection of organic chemical compounds spotted on a solid surface provides a tool to search proteins that bind with specific chemical compounds; the DNA microarray is the best known and most currently used microarray in biological and medical research, its applications include gene expression profiling, comparative genomic hybridization, GeneID, chromatin immunoprecipitation on chip, DamID, SNP detection, alternative splicing detection, fusion genes microarray, and tiling array; the protein microarray's applications include profiling protein abundance (known as analytical microarrays or capture arrays), and identifying protein-protein, protein-DNA, protein-RNA, protein-phospholipid, and protein-small molecule interactions (known as functional protein microarrays or target protein arrays). The formed probe-target hybridization is then detected and quantified by detection of fluorophore-, silver-, chemiluminescence-, affinity-, photochemical-, or radioisotope-labeled targets/probes to determine relative abundance of the molecules of interest. A number of label-free detection methods are also available, such as surface plasmon resonance (SPR), carbon nanotubes, carbon nanowire sensors (where detection occurs via changes in conductance) and microelectromechanical system (MEMS) cantilevers. In label-free technology, 3D result may be obtained.

For the convenience and clarity of explanation, RNA end-label microarray, such as miRNA microarray is chosen to be an example of DNA microarray hybridization-based platforms to explain the principle of the technology and the use of this innovation in microarray. DNA microarray technology evolved from Southern blotting, where fragmented DNA is attached to a substrate and then probed with a known DNA sequence. A DNA microarray is a collection of thousands of microscopic DNA spots attached to a solid surface. Each DNA spot contains picomoles ($10^{-12}$ moles) of a specific DNA sequence, known as probe (or reporters or oligonucleotides). These can be a short section of a gene or other DNA element that are used to hybridize a cDNA or cRNA (also called anti-sense RNA) sample (known as target) under hybridization conditions, unbound nucleic acid is then removed. Probe-target hybridization is then scanned in a microarray scanner to visualize fluorescence its intensity is correlated with the abundance of target of interest.

FIG. 1 provides a schematic representation of gene expression microarray technology. Labeled target 101 in target 100 binds to specific probe 201 fixed on the glass slide 200 through hybridization. The labeled fluorophore can be detected during scanning process and the scanned signal intensity at the location 201 represents the quantity of target RNA 101.

Figure 2:
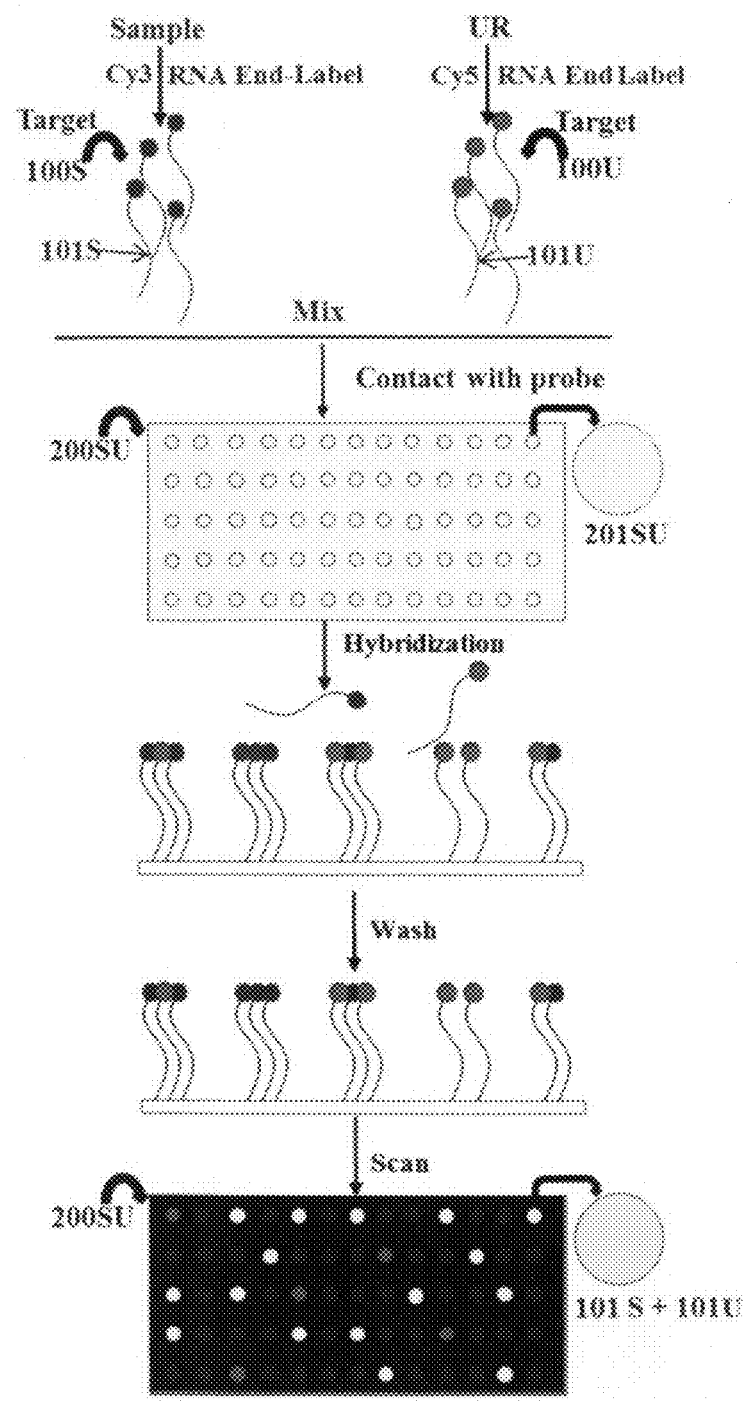
FIG. 2 provides a schematic representation of two-color gene expression microarray technology.

In order to have a baseline expression measure for each gene to enable normalization and comparison of independent experiments, UR and two-color labeling method was developed in microarray technology showing in FIG. 2.

FIG. 2 provides a schematic representation of two-color gene expression microarray technology. Cy-3 labeled target 101S in sample target 100S and Cy-5 labeled target 101U in UR target 100U bind to specific probe 201SU fixed on the glass slide 200SU through hybridization. The labeled fluorophore can be detected during scanning process and the scanned signal intensities at the location 201SU represent the quantity of sample target RNA 101S (green) and UR target 101U (red), respectively; color yellow indicates almost equal amount of green (101S) and red (101U).

However, UR and two-color labeling method cost twice and UR is not feasible to establish a true universal reference either. A better approach would be absolute quantification, which may be achieved if such a method is established that it performs simultaneous labeling and hybridization of the sample of interest and the standard reference that is used in the method can represent global miRNAs' characters.

Under the prior art methods, each experiment obtains a relative quantitative data because the direct absolute quantification of RNAs by the measured array signal intensity alone is impossible due to the sequence-dependent labeling and hybridization efficiencies of RNAs and the labeling and hybridization variations of each experiment (GIT et al. 2010, NOVORADOVSKAYA et al. 2004, BISSELS et al. 2009, SHI et al. 2010, DUDLEY et al. 2002, CARTER et al. 2005, BAKER 2010, LESHKOWITZ et al. 2013, RYDEN et al. 2006, BENES et al. 2003). Thus it is difficult to compare and integrate data of different experiments. To date, few experimental approaches have been developed to meet the quantification and data comparison requirements and spike-in is the most notable. In the prior art spike-in method involves printing a set of foreign control probes (no cross hybridization with the sample target of interest) (S-probe) onto the arrays and then adding their corresponding RNA (S-target) into the sample RNA of interest before labeling and hybridization (LOCKHART et al. 1996, BISSELS et al. 2009, CARTER et al. 2005, BAKER 2010, LESHKOWITZ et al. 2013, RYDEN et al. 2006, BENES et al. 2003, FARDIN et al. 2007, LEMIRE et al. 2011). Thus, spike-in cancels biases related to labeling and hybridization caused by variations of each experiment. In the prior art spike-in, the spike-in target is the one with known amount.

Figure 3:
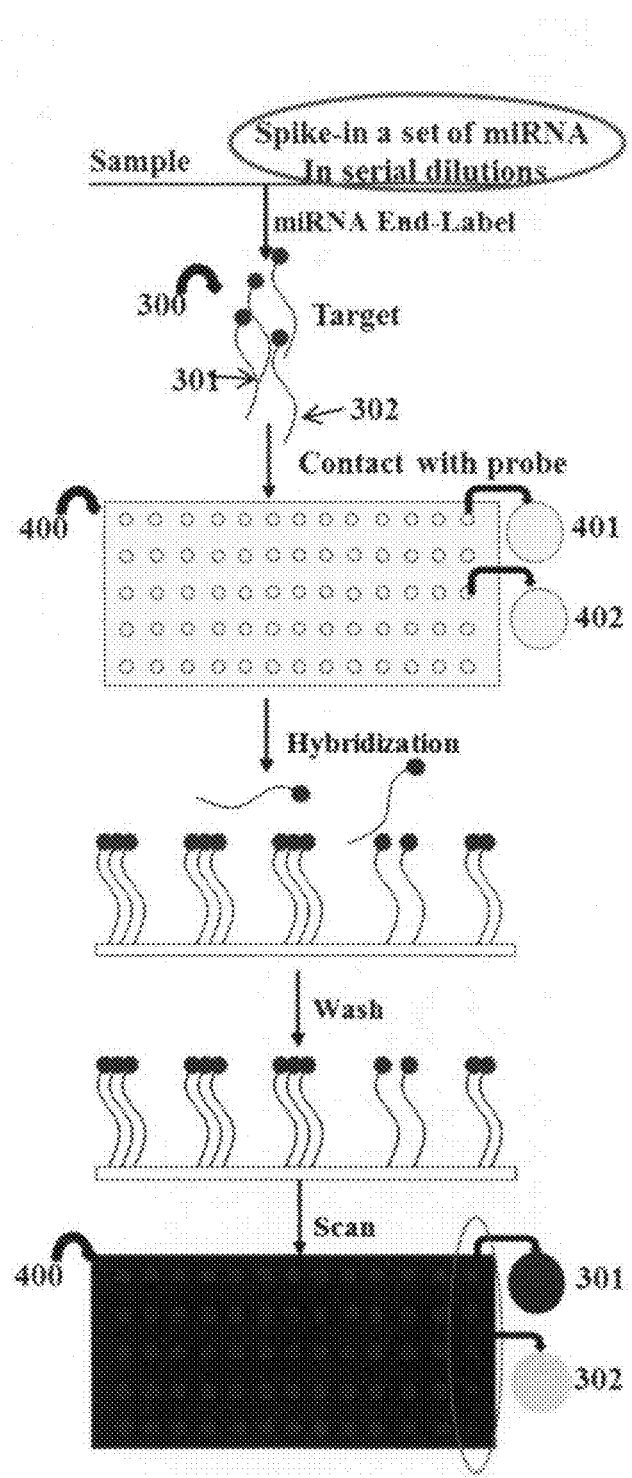
FIG. 3 provides a schematic representation of spike-in method in gene expression microarray technology.

FIG. 3 provides a schematic representation of spike-in method in gene microarray technology. Labeled spike-in foreign miRNA 301 and 302 (which are S-targets) in the mix of target 300 (that is the sample miRNA of interest) bind to specific probe 401 and 402 (which are S-probes) fixed on the glass slide 400 through hybridization, respectively. The miRNA 301 and 302 are spiked-in at different abundance; probe 401 and 402 are fixed on the glass slide with the same abundance. The labeled fluorophore can be detected during scanning process and the scanned signal intensity at the location 401 and 402 represent the quantity of S-target 301 and 302, respectively. This method has been widely used in microarray quality control and relative quantification analysis.

Carter et al. demonstrated that spike-in can be used to perform absolute quantification of endogenous RNA expression (CARTER et al. 2005). They used seven yeast mRNA sequences as exogenous mRNA controls (S-target). Gene expression profiles were generated for triplicate total RNA samples from mouse embryo, placenta, ES cells, and TS cells with yeast sequence (S-targets) spike-in at different known copy numbers. A linear regression analysis was performed on those S-target mean normalized $\log_{10}$ [intensity] values for each microarray. The regression line for the average of all tissues was shown in dashed line and its equation was used to back-calculate estimated copy numbers for endogenous transcripts as $C_{hmi}=(l_i-a)/b$, where $C_{hmi}$ is the microarray-estimated number of copies per hybridization for probe i, $l_i$ is the normalized $\log_{10}$ [intensity] for probe i, and a and b are the intercept and slope of S-targets as shown in FIG. 4.

Figure 4:
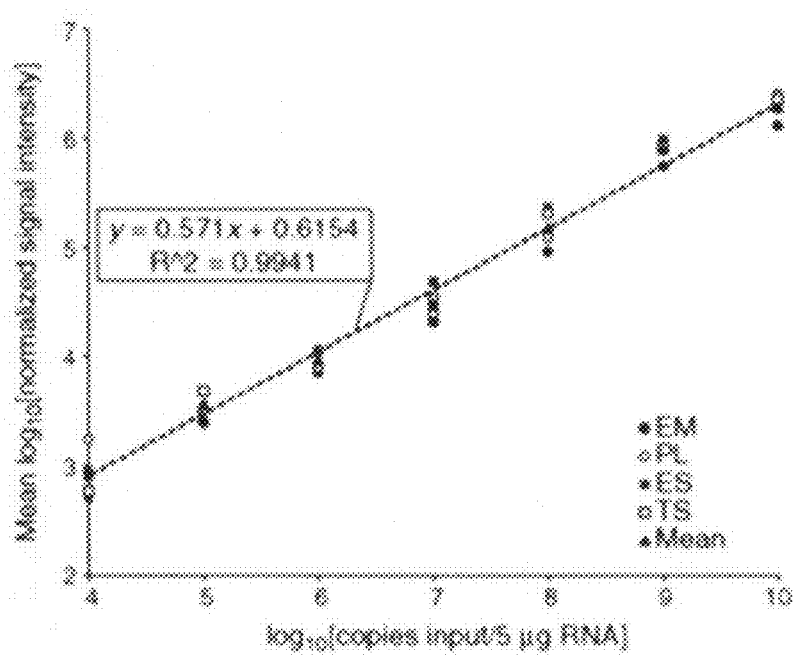
FIG. 4 provides an example of spike-in method in gene expression microarray technology to assay the copy number of sample of interest.

FIG. 4 provides an example of spike-in method in gene expression microarray technology to assay the copy number of sample of interest. This work was done by Carter et al. FIG. 4 is the original FIG. 2b in the publication (CARTER et al. 2005). The linear regression of seven yeast S-target copy number to mean microarray signal intensity spiked-in mouse RNAs of embryo, placenta, ES cells and TS cells shows very robust microarray signal intensity-copy number correlations, with $r^2$ value of 0.99.

For accurate normalization among individual experiments, however, the S-target concentrations must be precise across all the samples using the prior art spike-in method which Carter used (ZHOU et al. 2012, CARTER et al. 2005, BENES et al. 2003, FARDIN et al. 2007, LEMIRE et al. 2011); this is often challenging and it has been rarely used in gene copy number assay. Another shortcoming of the prior art spike-in is that one S-target sequence only generates one intensity data in an array; a linear regression can only be made on the combination of S-target sequences. Thus one standard curve for all endogenous RNA normalization is not feasible because it cannot reflect the linear dynamic range of sequences with different attributes, therefore, the standard reference cannot represent global RNAs' characters. Yet another shortcoming of the prior art spike-in is that it cannot reflect the difference of labeling amount caused by different gene sequences. Therefore, the first need is to innovate the prior art spike-in method from the individual controlled amount to centralized quality control to guarantee the amount of spike-in reference being equal among all measured samples. To achieve this goal, the best approach is to standardize the S-probe via manufacture process which in turn control the amount of S-target because the one to one molecule binding ratio between probe and target.

The feasibility of the above idea of using fixed probe to control spike-in amount is experimentally proved by a published data of Yauk et al. in 2006 (YAUK et al. 2006). In order to find a better quality assurance and/or normalization features for their specific toxicogenomics microarray, they designed an alternative method of microarray control compared to commercial available microarray. Contrary to the general practice that employs the prior art spike-in method described before, they tested the possibility of a method that uses a single external control spike-in concentration of one RNA sequence, but hybridizes against spotted dilutions of the complimentary probes printed on the array. Using *Arabidopsis thaliana* chlorophyll synthase gene, they performed reciprocal dilution experiments to determine the extent to which on-chip probe concentrations were mimics of the effects of variable concentrations of the solution-phase cRNA partner in bimolecular hybridization reactions. The chlorophyll synthase cRNA was spike-in a single concentration (5 ng) with mouse RNA (5 µg) and hybridized against spotted dilutions (0.000015 to 100 µM, covered from background to saturation) of its probe on an array; reciprocally, dilution series of the spike-in reference cRNA were made in solutions with mouse RNAs and hybridized to multiple arrays. The result was shown in FIG. 5 (also the original FIG. 5 in the publication).

Figure 5:
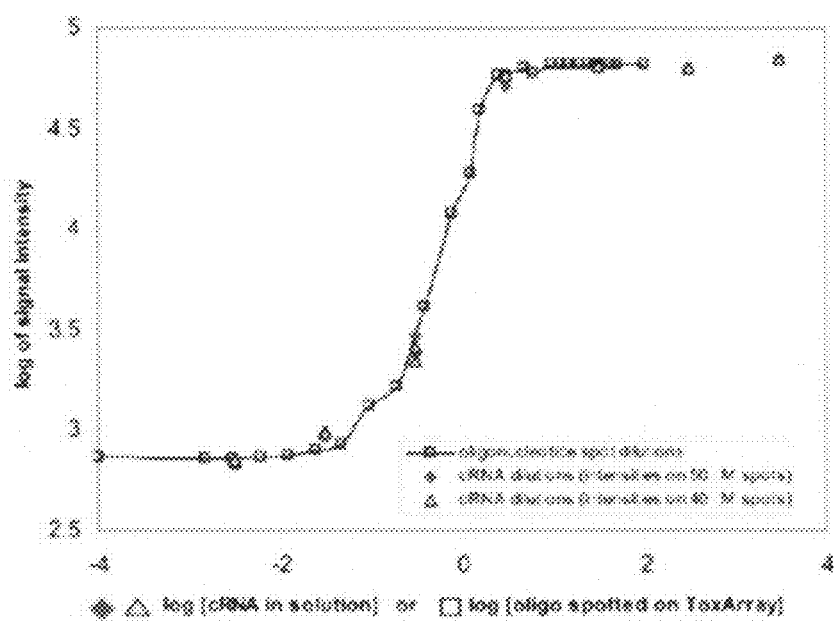
FIG. 5 demonstrates the feasibility that hybridization of the spotted dilution series with a single spike-in concentration of external RNA produced identical profiles of signal intensities compared to the signals obtained from serial spike-in dilutions of the external reference RNA.

FIG. 5 demonstrates the feasibility that hybridization of the spotted dilution series with a single spike-in concentration of external RNA produced identical profiles of signal intensities compared to the signals obtained from serial spike-in dilutions of the external reference RNA (YAUK et al. 2006).

However, Yauk's method cannot be used in absolute quantification because no reference with absolute quantity can be defined in the publication. Their purpose of developing this reverse series of reference is well expressed in their summary quoted from the publication: "The design and placement of the series allows for QA (quality assurance) examination of frequently encountered problems in hybridization and printing. Additionally, we demonstrate that the series can be integrated with a LOWESS normalization to improve the detection of differential gene expression (improved sensitivity and predictivity) over LOWESS normalization on its own." (YAUK et al. 2006) Yauk et al. pointed out that their major goal was to satisfy the need of quality assurance; as a minor effect, the design could improve the detection of differential gene expression that is relative quantification, when used with LOWESS normalization together. The relative quantification of Yauk's method was done mainly depended on UR with two-color system, and the reverse series of reference could only be used to improve the detection of differential gene expression.

Although abandoned by Yauk et al. in their later publications (ALVO et al. 2010, MALIK et al. 2012), reverse control has certain advantages: 1) It is easy to standardize the reference as it can be manufactured on the array. 2) More than one standard curves can be developed on the same array chip to better represent global RNAs' characters. For those reasons, reverse dilution is employed to develop absolutely quantitative microarray to innovate the current general practice of relative quantification via manufactured built-in standard curve in the following.

In order to distinguish from the prior art spike-in, the spike-in employed in the present application to develop a universal absolute copy number standard curve will be named SS-spike-in (single saturated spike-in amount). Probes corresponding to the SS-spike-in (SS-probe) will be printed on an array with serial copy number dilutions which span signal intensities from near background to saturation. SS-spike-in foreign biological molecule (SS-target) which has no cross hybridization with the target biological molecule of interest will be added into the experiment sample in the amount of more than 1× total SS-probe copy numbers on the array chip.

Figure 6:
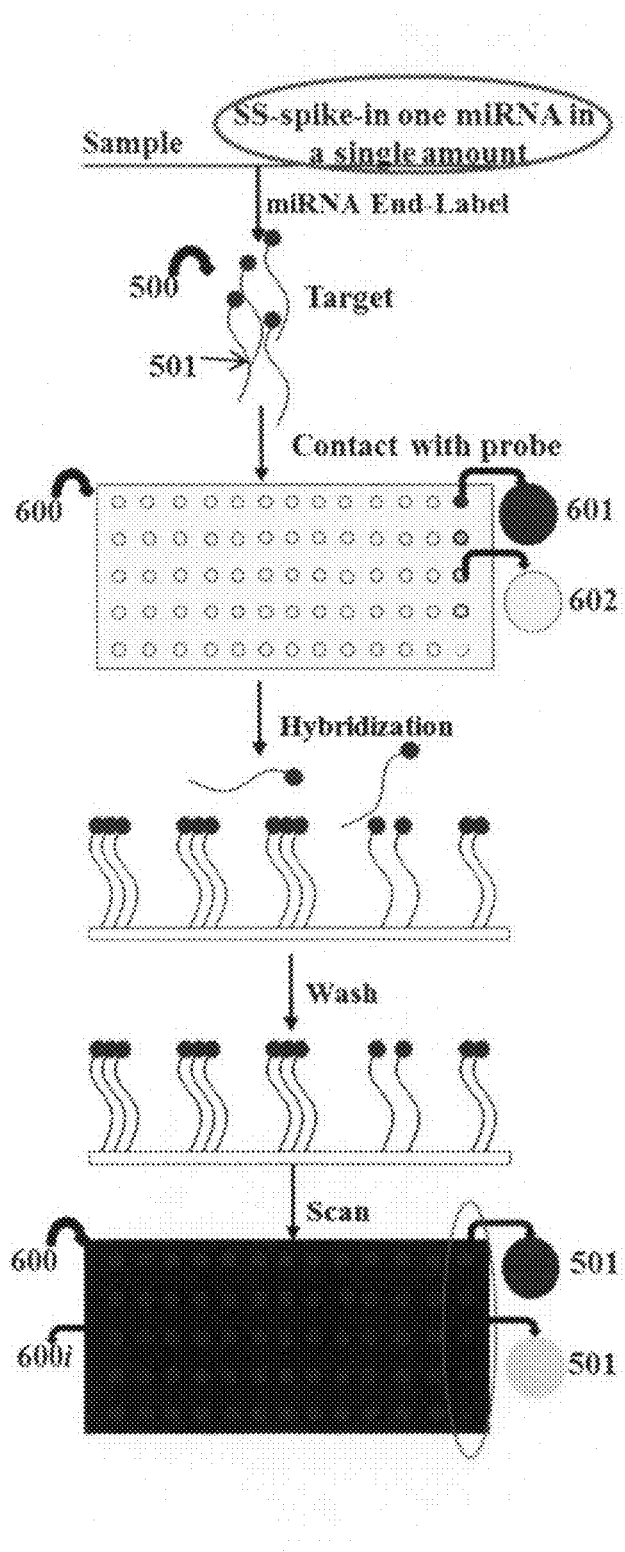
FIG. 6 provides a schematic representation of built-in standard curve with a single saturated spike-in amount (SS-target) method (SS-spike-in) in end-labeling microarray technology (labeling method one).

FIG. 6 provides a schematic representation of built-in standard curve with SS-spike-in method in end-labeling microarray technology. Labeled SS-spike-in miRNA 501 (SS-target) with a single amount in the mix of target 500 (SS-target) binds to specific probe spots with serial dilutions, such as spot 601 and 602 (SS-probe) fixed on the glass slide 600 through hybridization. Spot 601 and 602 have the same sequence that corresponding to SS-target 501, but with different copy numbers. The labeled fluorophore can be detected during scanning process and the scanned signal intensity at the location 601 and 602 represent the quantity of SS-target 501 as known copy numbers of SS-probe 601 and 602, respectively.

Linear regression analysis of SS-target signal and SS-probe is used to define a standard curve relating signal intensity to copy number. Determination of endogenous miRNA copy number of target 500 will be back-calculated according to the formula obtained from the regression analysis of standard curve. FIG. 6 illustrates that one SS-target can generate one standard curve. Multiple standard curves representing different attributes may be generated on the same array by employing different SS-targets and SS-probes.

For protein microarray, the capture molecules arrayed on the solid surface may be antibodies, antigens, aptamers (nucleic acid-based ligands), affibodies (small molecules engineered to mimic monoclonal antibodies), or full length proteins. The technology principle of antibodies as capture molecules is illustrated in the section of ELISA. The principle of SS-spike-in method is the same as described above, but the arrayed capture molecules in serial dilutions are antibodies, antigens, aptamers, affibodies, or full length proteins.

II. PCR Array

The PCR is a biochemical technology in molecular biology used to amplify a single or a few copies of a piece of DNA across several orders of magnitude. The DNA which is amplified is called template (It is a target) for PCR reaction. The quantitative PCR (qPCR) methods allow the estimation of the amount of a given sequence present in a sample, the template, a technique often applied to quantitatively determine levels of gene expression. qPCR is an established tool for DNA quantification that measures the accumulation of DNA product after each cycle of PCR amplification. This technology is very well known in the art, thus, the detail description of the technique is omitted, but mention of that a pair of primers (They are probes, which detect and amplify targets) decide the sequence specificity and length of amplicon.

There are two detection formats in qPCR: double-stranded DNA (dsDNA) dye based or probe based (This probe detects PCR product abundance). SYBR Green I is one of dsDNA-binding dye. It binds to the minor groove of dsDNA and upon binding increases in fluorescence over a hundred fold. Thus, fluorescence measurement at the end of the elongation step of every PCR cycle can monitor the increasing amount of amplified DNA to provide an excellent tool for specific product identification and quantification. Probe based qPCR relies on the sequence-specific detection of a desired PCR product. It utilizes a fluorescent-labeled target-specific probe, such as TaqMan probe, resulting fluorescence signal permits quantitative measurements of the accumulation of the product during the exponential stages of the PCR (MACKAY 2002, BioSearch Technologies, BENGTSSON et al. 2003, WITTWER et al. 1997, National Center for Biotechnology Information (NCBI) Probe Database, HOLLAND et al. 1991).

Figure 7:
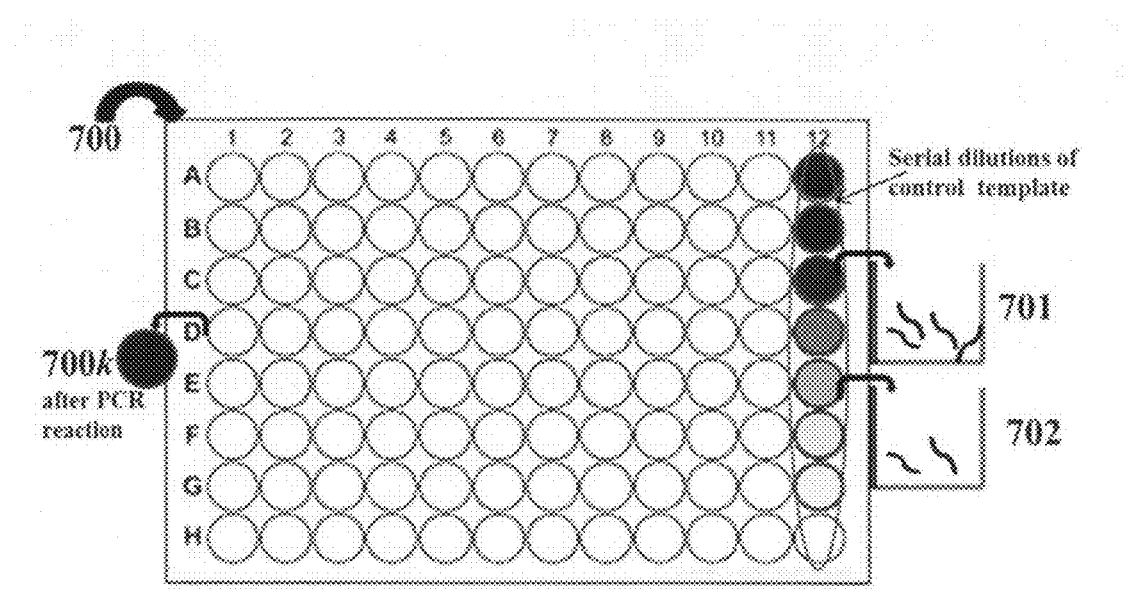
FIG. 7 illustrates how built-in standard curve is used in quantitative PCR.

FIG. 7 illustrates how built-in standard curve is used in quantitative PCR. The DNA template of control is pre-spotted in multiple-well plate in serial dilutions, such as 701 and 702 on 96-well plate 700. The detected signal by real-time PCR (real-time PCR is qPCR) machine, such as QuantStudio™ Real-Time PCR system, will be subjected to linear regression analysis on control template to define standard curve relating signal intensity to copy number. Determination of the copy number of sample of interest will be back-calculated the endogenous miRNA copy number of target 500 according to the formula obtained from the regression analysis of standard curve. Since each reaction is isolated in a well, the control template sequence can be exogenous or endogenous.

III. ELISA Array and Membrane Based Array

The principle of enzyme-linked immunosorbent assay (ELISA) is a test that uses antibodies and color change to identify an "analyte". Performing an ELISA involves at least one antibody with specificity for a particular antigen. The sample with an unknown amount of antigen is immobilized on a solid support (usually a polystyrene multiple-well plate) either non-specifically (via adsorption to the surface) or specifically (via capture by another antibody specific to the same antigen, in a "sandwich" ELISA). After the antigen is immobilized, the detection antibody is added, forming a complex with the antigen. The detection antibody can be covalently linked to an enzyme, or can itself be detected by a secondary antibody that is linked to an enzyme through bioconjugation. Between each step, the plate is typically washed with a mild detergent solution to remove any proteins or antibodies that are non-specifically bounded. After the final wash step, the plate is developed by adding an enzymatic substrate to produce a visible signal, which indicates the quantity of antigen in the sample. ELISA is performed by methods that stay liquid and remain inside a reaction chamber or well needed to keep the reactants contained. The types of ELISA include: direct ELISA that the antigen to be tested is immobilized to each well of a multiple-well plate, "indirect" ELISA (sandwich ELISA that is illustrated in FIG. 8), competitive ELISA (such as cumulative competition occurs between the two antibodies for the same antigen, causing a stronger signal to be seen.), or simultaneous detection of different antibodies and antigens.

The principle of membrane based array (antibody array) is similar to western blot, but pre-immobilized antibodies on the membrane. Thus, all detection methods which are useful for western blot can be used in membrane based array, such as colorimetric detection, chemiluminescent detection, radioactive detection, and fluorescent detection. Since membrane based array belongs to protein immunoblot, it submits to the same principle of immunoreaction of ELISA.

Figure 8:
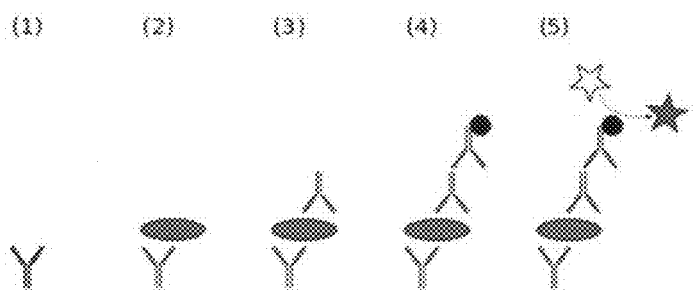
FIG. 8 illustrates the principle of sandwiched immunoassay.

FIG. 8 illustrates the principle of sandwiched immunoassay. (1) Plate/membrane is coated with a capture antibody; (2) sample is added, and any antigen present binds to capture antibody; (3) detecting antibody is added, and binds to antigen; (4) enzyme-linked secondary antibody is added, and binds to detecting antibody; (5) substrate is added and is converted by enzyme to detectable form.

Figure 9:
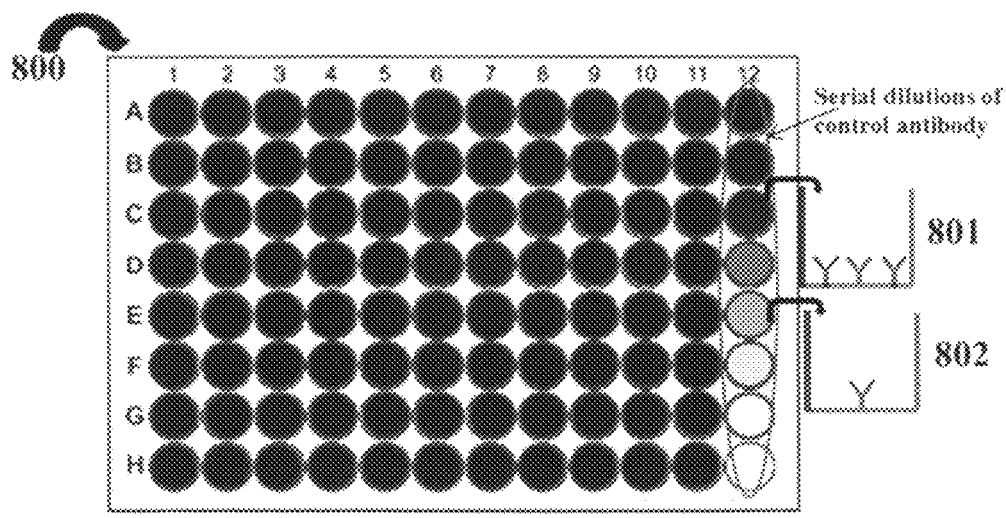
FIG. 9 illustrates how built-in standard curve is used in sandwich ELISA.

FIG. 9 illustrates how built-in standard curve is used in sandwich ELISA. The capture antibody of control is pre-immobilized in multiple-well plate in serial dilutions, such as 801 and 802 on 96-well plate 800 to generate a standard curve. The antibodies of sample of interest are pre-immobilized in multiple-well plate in saturated amount. The detected signal by plate reader will be subjected to linear regression analysis on control wells to define standard curve relating signal intensity to copy number. Determination of the copy number of sample of interest will be back-calculated according to the formula obtained from the regression analysis of standard curve. Since each reaction is isolated in a well, the capture antibody of control may or may not be the sample of interest.

Figure 10:
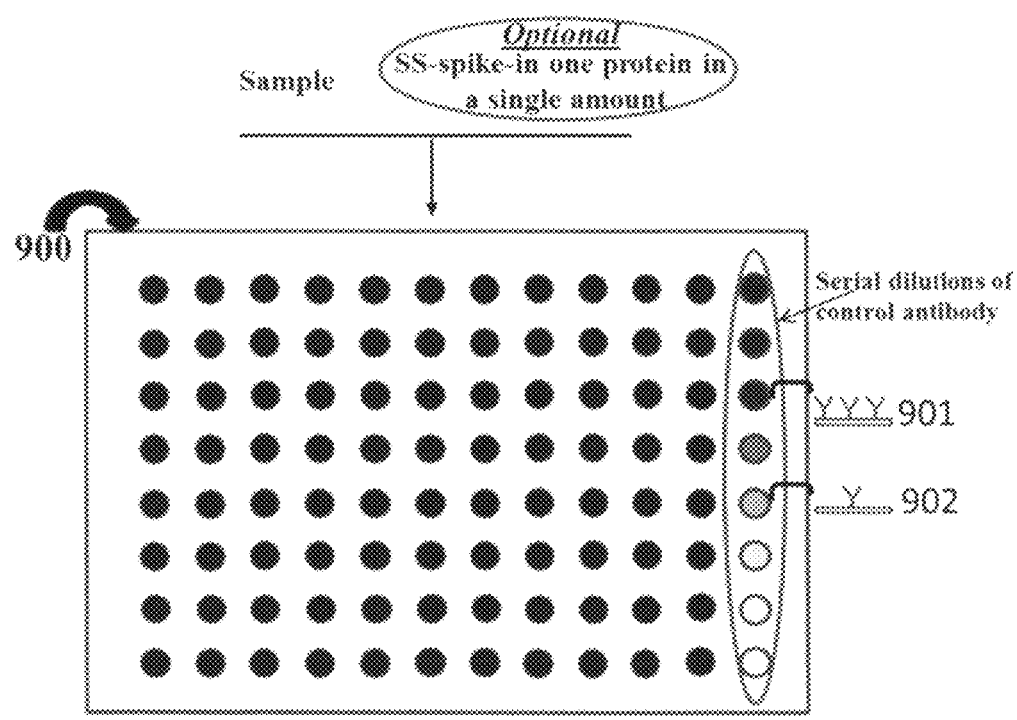
FIG. 10 illustrates how built-in standard curve is used in sandwich membrane antibody array.

FIG. 10 illustrates how built-in standard curve is used in sandwich membrane antibody array. The capture antibody of control is pre-spotted on the membrane, (e.g. nitrocellulose/PVDF membrane) in serial dilutions, such as 901 and 902 on nitrocellulose membrane 900 to generate a standard curve. Chemiluminescence signal is detected in the same manner as a western blot. The detected signal will be subjected to linear regression analysis on control to define standard curve relating signal intensity to copy number. Determination of the copy number of sample interest will be back-calculated according to the formula obtained from the regression analysis of standard curve. The capture antibody of control should not have cross-binding with the sample interest, but may be endogenous or exogenous.

IV. Calculating Signal Intensity Unit and Various Labeling Methods

Although SS-spike-in method can solve the problem of standardizing the reference amount via engineering serial dilutions of SS-probe and may represent different RNA characters via engineering more than one standard curves, SS-spike-in alone still cannot reflect the difference of signal intensity of different molecule. Thus, it is yet a need to compare each molecule at the precise same level among sample and control. That goal will be achieved via computational method described in the following.

Another feature of the present application is to translate the detected signal intensity to signal intensity unit (IU). The IU is per detectable unit per copy of molecule. The concept of IU is introduced to define the equality between the sample of interest and the SS-spike-in, and the equality among the sample of interest and among the SS-spike-in. The purpose of IU is to allow mathematic calculations (regression analysis of standard curve and back-calculation of copy number of sample) can be performed on the precise same level.

A) When label methods are used, IU is the signal emitted from per basic labeling unit per copy of molecule. The basic labeling unit can be a molecule that emits/re-emits a detectable signal, such as a fluorophore that re-emits light upon light excitation; the basic labeling unit can be a molecule that generates a detectable signal via metabolizing a substrate, such as an enzyme to cleave a chemiluminescent agent to produce luminescence, or to convert a substrate to a detectable color; the basic labeling unit can be a molecule that serves as a link between the molecule of interest and the molecule that causes detectable signal, such as a biotin that can be covalently attached to a protein of interest and then the biotin tag can be recognized by a gold-coupled anti-biotin conjugate that can cause detectable silver precipitation spot.

Three different labeling/dyeing methods are used to explain how IU is obtained based on the measured signal intensity in the following; control is SS-spike-in, and sample is the sample of interest:

1) Labeling method one: One basic labeling unit per molecule of interest, such as miRNA end labeling in miRNA microarray in FIG. 6; fluorogenic-labeled probes in qPCR in FIG. 7; or same labeling amount per biological molecule interest, such as an enzyme covalently linked to the second antibody in "sandwich" ELISA or membrane antibody array in FIG. 8, FIG. 9 and FIG. 10. Each molecule of sample and molecule of control is capable of generating the same signal of known value.

$$IU_C = \frac{INTENSITY_C}{CN_C}$$

Is the formula to calculate the IU of control ($IU_C$); $INTENSITY_C$ (the signal intensity of control), and $CN_C$ (the copy number of control).

$$IU_S = \frac{INTENSITY_S}{CN_S}$$

Is the formula to calculate the IU of sample ($IU_S$); $INTENSITY_S$ (the signal intensity of sample), and $CN_S$ (the copy number of sample).

In labeling method one, per biological copy number generates same signal intensity. Thus, if $CN_S = CN_C$, then $INTENSITY_S = INTENSITY_C$.

2) Labeling method two: Unequal number of basic labeling unit per molecule of interest, such as Cy3-CTP labeled cRNA in mRNA expression profile microarray in FIG. 11. The individual labeled nucleotides on the molecule of control and on the molecule of sample are all capable of generating the same signal of known value.

$$IU_C = \left(\frac{INTENSITY_C}{NL_C}\right)/CN_C$$

Is the formula to calculate the IU of control ($IU_C$); $INTENSITY_C$ (the signal intensity of control), $CN_C$ (the copy number of control), and $NL_C$ (number of basic labeling units per control molecule).

$$IU_S = \left(\frac{INTENSITY_S}{NL_S}\right)/CN_S$$

Is the formula to calculate the IU of sample ($IU_S$); $INTENSITY_S$ (the signal intensity of sample), $CN_S$ (the copy number of sample), and $NL_S$ (number of basic labeling units per sample molecule).

In the labeling method two, per copy number of each gene of the sample of interest may generate different signal intensity, and may be different from the signal intensity of per copy number of control. In labeling method two, the signal intensity of per copy number depends on the total number of basic labeling units that bind to the biological molecule.

Figure 12:
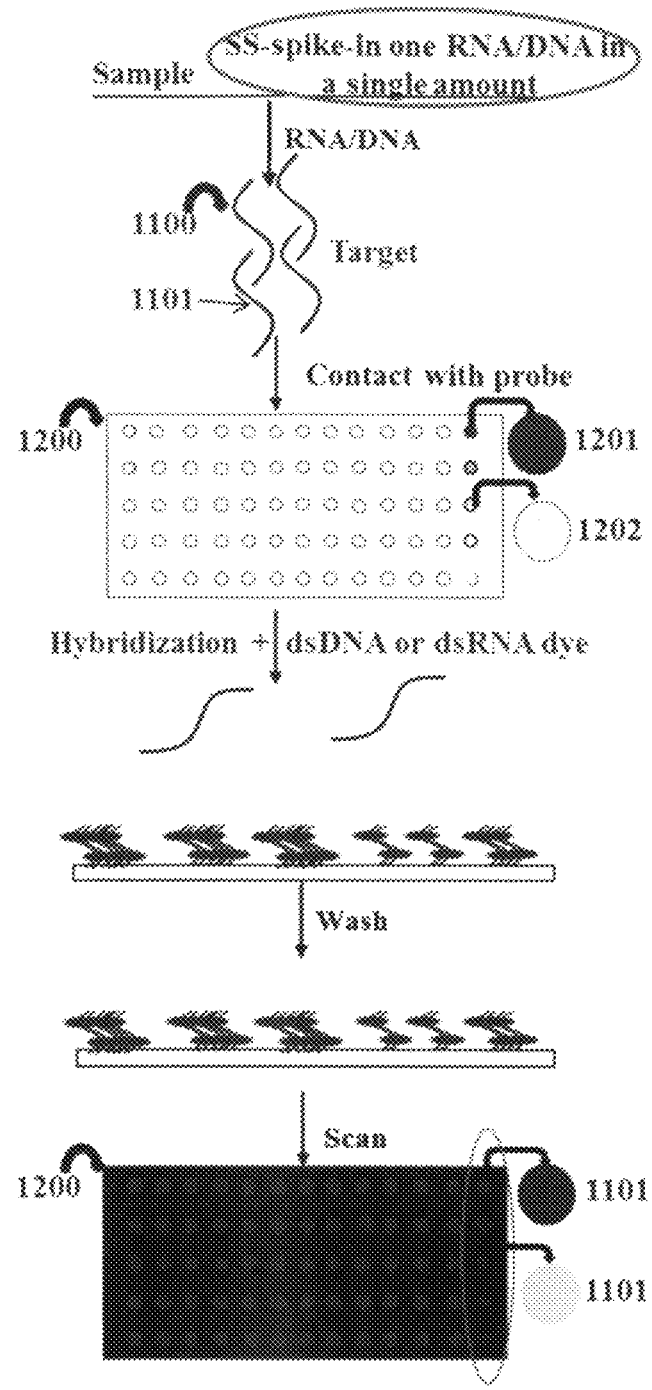
FIG. 12 provides a schematic representation of built-in standard curve with SS-spike-in method in dsDNA/dsRNA dye staining microarray technology (labeling method three).

3) Labeling method three: The basic labeling unit is a double-stranded DNA/RNA binding dye, such as SYBR Green I, PicoGreen, EvaGreen, Hoechst 33258, BEBO, QuantiFluor, AccuClear, or AccuBlue. The dye binds dsDNA in qPCR products in FIG. 7, or in microarray hybridization pattern in FIG. 12. Each individual hybridized A-T/C-G of dsDNA is capable of binding the same amount of basic labeling unit, thus, each A-T/C-G is capable of generating the same signal of known value.

$$IU_C = \left(\frac{INTENSITY_C}{NN_C}\right)/CN_C$$

Is the formula to calculate the IU of control ($IU_C$); $INTENSITY_C$ (the signal intensity of control), $CN_C$ (the copy number of control), and $NN_C$ (the number of nucleotides per control molecule).

$$IU_S = \left(\frac{INTENSITY_S}{NN_S}\right)/CN_S$$

Is the formula to calculate the IU of sample ($IU_S$); INTENSITYS (the signal intensity of sample), $CN_S$ (the copy number of sample), and $NN_S$ (the number of nucleotides per sample molecule).

In labeling method three, per copy number of each gene of the sample of interest may generate different signal intensity, and may be different from the signal intensity of per copy number of control. In labeling method three, the signal intensity of per copy number depends on the sequence length (nucleotide number) of double-stranded molecules; the longer, the stronger of signal intensity.

B) When label-free technology is used, IU is the signal emitted from per basic building unit per copy of molecule. For example, amino acids are the building units of protein; nucleotides are the building units of DNA. Label-free biosensor technology is a well-established analytical tool for kinetic, affinity, and concentration analyses; its application in a high-throughput setting has also been geared up (RICH et al. 2007, LIEDBERG et al. 1983). Label-free technologies include surface plasmon resonance (SPR), nuclear magnetic resonance (NMR), high-throughput mass spectrometry, resonant waveguide plate-based screening, transmitted-light imaging, isothermal titration calorimetry, optical and impedance cell-based assays and other biophysical methods. In an optical biosensor experiment, a population of one binding partner is tethered to a sensor surface and an aliquot of the other partner is injected across this surface. The optical detection system measures the change in refractive index of the buffer near the sensor surface as analyte mass accumulates on the surface (RICH et al. 2007, LIEDBERG et al. 1983, O'MALLEY et al. 2007, WEMMER 2000). By measuring reflectivity, SPR can detect molecular adsorption, such as polymers, DNA or proteins, aptamer-protein interactions, etc. When the surface is patterned with different biopolymers, using adequate optics and imaging sensors (i.e. a camera), the technique extends to be surface plasmon resonance imaging (SPRI). SPRI provides a high contrast of the images based on the adsorbed amount of molecules, such as in antibody-polypeptide microarray in which the specific profile of antibody-polypeptide binding are determined by three-dimensional histogram (BROOKS et al. 2014, CHEN et al. 2012), and aptamer-protein microarray (Lautner et al.).

In label-free method, the calculation formulas of IU are the same of labeling method three. But $NN_C$ can be the number of nucleotides, or the number of amino acids, or the number of other basic building units of the molecule of interest; $NN_S$ can be the number of nucleotides, or the number of amino acids, or the number of other basic building units of the molecule of interest. Those formulas are based on the assumption of that each nucleotide/each amino acid/each other basic building unit can generate same signal of known value to meet the concept that IU has equality between the sample of interest and the SS-spike-in. Should this assumption be breached by scientific discovery, the formulas should be modified according to the scientific discovery.

V. Mathematic Formula for Various Labeling Methods

Figure 13:
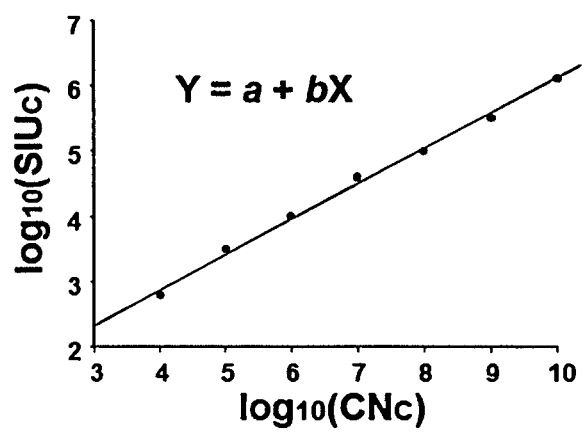
FIG. 13 provides a putative standard curve and linear regression equation resulting from the use of a serial dilution of pre-engineered probe (SS-probe) and the complementary SS-target technology.

FIG. 13 showing how regression analysis will be performed using control signal intensity and the known copy number on each location of control spot/well to derive a standard curve. This example applies simple linear regression analysis to generate equation Y=a +bX; where X is the $\log_{10}$ transformed copy number ($CN_C$), and Y is the sum of total $IU_C$ ($SIU_C$) for a giving spot/well which is also $\log_{10}$ transformed, b is the slope of the line, and a is the intercept. Thus, the copy number of a sample interest can be calculated by: $X=10^{(Y-a)/b}$; where X is the copy number of sample interest ($CN_S$), and Y is the sum of total $IU_S$ ($SIU_S$) for a giving spot/well which is $\log_{10}$ transformed.

Since SIU=IU×CN, therefore—

In labeling method one, $SIU_S$=$INTENSITY_S$=$SIU_C$=$INTENSITY_C$ when $CN_S$=$CN_C$;

In labeling method two, $SIU_S$ $INTENSITY_S$, $SIU_C$ $INTENSITY_C$, $SIU_C$=/≠$SIU_C$ even $CN_S$=$CN_C$, depending on whether $NL_S$=$NL_C$ or not;

In labeling method three, $SIU_S$<$INTENSITY_S$, $SIU_C$<$INTENSITY_C$, $SIU_S$=/≠$SIU_C$ even $CN_S$=$CN_C$, depending on whether $NN_S$=$NN_C$ or not.

The built-in standard curve can be one or more per array/plate/membrane; the control molecule can be a single molecule or many different molecules.

VI. The Computer Software and Kits of the Invention

Figure 14:
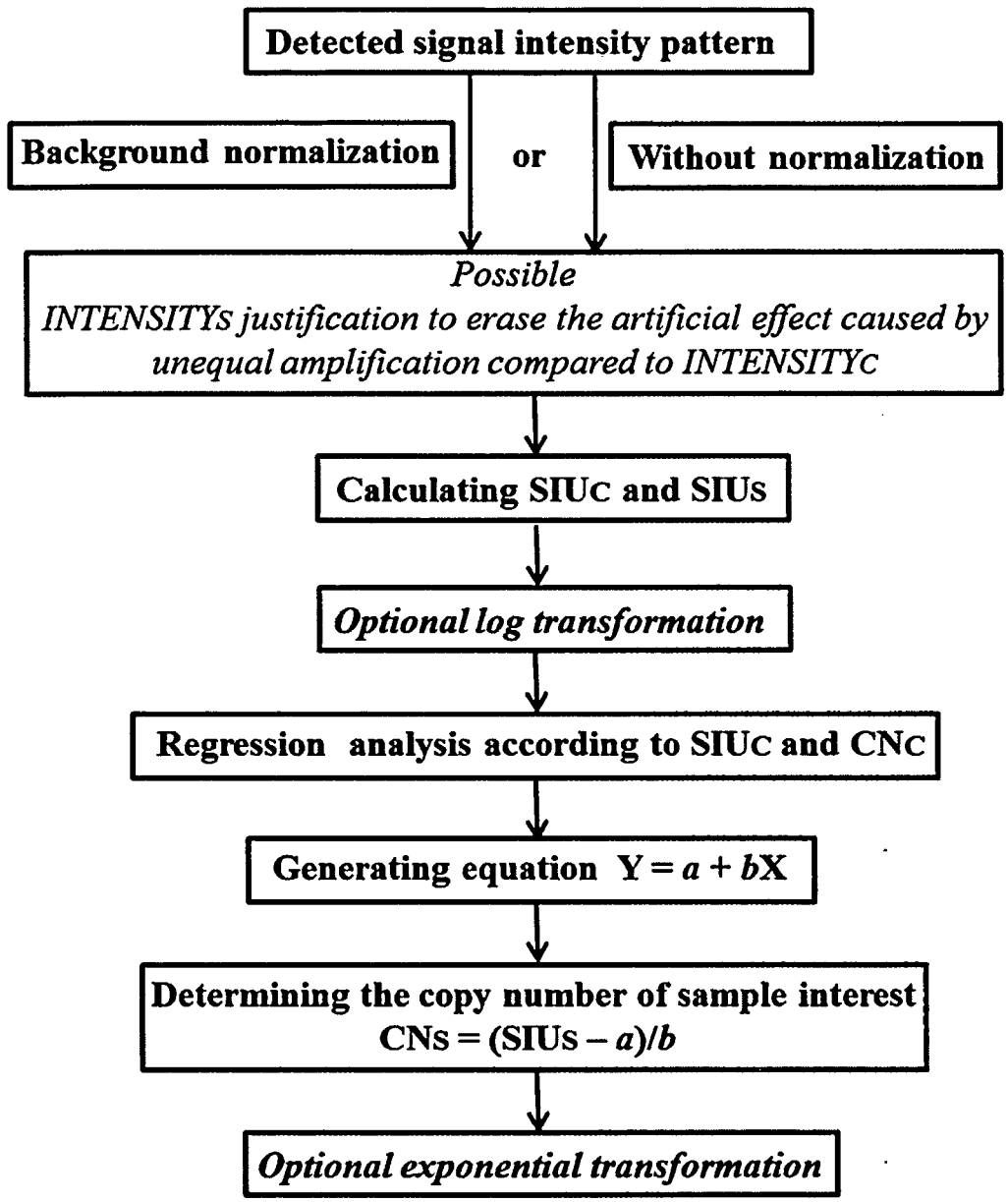

In another embodiment of the invention, computer software for carrying out the subject invention is provided. FIG. 14 illustrates how the computer software is composed in a diagram. Such software may include normalization of background noise, normalization of hybridization on different locations (for example, each sub-grid) of a array, normalization of dye intensity, logarithm transformation of signal intensity and copy number, calculation of $IU_C$/$SIU_C$ and $IU_S$/$SIU_S$ according to measured signal intensity pattern, creation of standard curve(s) according to $IU_C$/$SIU_C$ and $CN_C$, generation of mathematic equation(s) according to the standard curve(s), determination of the copy number/absolute amount of each biological molecular interest. Such software may also include signal intensity justification for the subject that unequal amplification (e.g. PCR amplification) effect is involved between built-in control and the sample interest. Such software may be used on the computer connected with biological experiment device or on a remote computer for analysis of transferred biological experiment data.

In yet another embodiment of the invention, a kit and/or SS-Spike-in RNA, DNA, or peptide/protein, useful for the generating built-in standard curve(s) as described above, is provided. The kit and/or SS-spike-in set typically comprise a container, a label, and SS-target(s)/or SS-spike-in probe(s) as described above. The kit may further include other materials desirable from a commercial and user standpoint, including elements or devices designed to facilitate the introduction of the built-in standard curve(s) into the absolute quantification, other buffers, enzymes, dNTPs, diluents, filters, and the like. Such kit also includes instructional material for carrying out the subject methodology, where the instructional material could be present on a package insert, on one or more containers in kit and/or packaging associated with the kit.

In yet another aspect, the implementations include kit(s) which contain the adequate biological reagents to perform the assay. The term "biological reagent" as used herein refers to a biological material used for various biological analyses such as detecting, examining, and/or measuring information from biological samples.

In summary, the present invention provides an effective approach to assay the biological copy number via utilizing the common feature of biosensor detection system of selective interaction of certain biological molecules. Furthermore, the present invention takes advantage of constant ratio of the binding between probe and target. Therefore, it is possible to determine the molecule copy number of biological interest by pre-engineered standard copy number of either probe or target of control. Combed with computational method, precise determination of molecule copy number of biological interest is feasible. It may greatly contribute to the biomedical research by dramatically increasing the power of data to assist scientific discovery through global and historical data integration. It may greatly contribute to the clinical application as the data generated by experiments are applicable to clinical directly and there is no other translational step needed between researches and clinical. It may greatly contribute to cost efficiency because every data generated by standard can be repeatedly used, and because working efficiency can be improved by decreased individual experimental burden.

The following examples are offered by way of illustration and not by way of limitation. It is also to be understood that the following examples are focus on the use of this invention, not on the matured biosensor detecting systems as they are adopted entirely from those standard methods in the arts.

It is to be understood that the embodiments of the present invention which have been described are merely illustrative of some of the applications of the principles of the present invention. Numerous modifications may be made by those skilled in the art based upon the teachings presented herein without departing from the true spirit and scope of the invention. The contents of all references cited throughout this application are hereby incorporated by reference in their entirety for all purposes.

The following examples are set forth as being representative of the present invention. These examples are not to be construed as limiting the scope of the invention as these and other equivalent embodiments will be apparent in view of the present disclosure, figures and accompanying claims.

EXAMPLE

1. Human miRNA microarray and FIG. 6 are employed to serve as an example to explain how built-in standard curve is used in the labeling method one to assay the miRNA copy number profile of the biological sample of interest.

Foreign miRNA chosen to engineer standard curve: The mature sequence dme-miR-2a-1-5p of *drosophila* miRNA (miRBase accession number MIMAT0020780) is employed to generate a built-in standard curve on human miRNA microarray. The sequence of dme-miR-2a-1-5p is synthesized, purified and quantitated to be ready as SS-target 501.

The probe of standard curve: The complementary antisense oligonucleotides DNA of dme-miR-2a-1-5p with an extra "G" residue at the 5' end is synthesized, purified and quantitated to be ready as SS-probe. The SS-probe is then printed on the standard 1"×3" microscope glass slide surface, which is activated to be able to immobilize the oligonucleotides, in triplicates with serial copy number dilutions (range from $10^3$ to $10^{10}$ copies) using SurePrint inkjet technology. The spot 601 and 602 are examples of SS-probe spots, along with printed spots of human miRNA probes on the same slide.

SS-spike-in: The *drosophila* miRNA dme-miR-2a-1-5p, defined as SS-target 501, is added to 100 ng total human RNA sample with the amount of 2× of SS-probe copy number that is printed on the glass slides, which is $2\times3\times(10^3+10^4+10^5+10^6+10^7+10^8+10^9+10^{10})$ copies.

Labeling: The human total RNA with the SS-target 501 is subjected to miRNA 3' end-labeled with cyanine 3-pCp.

Hybridization: The labeled miRNA is added into the chamber that is loaded with a microarray slide for hybridization.

Washing: The hybridized microarray slide is washed using washing buffer.

Scanning: The hybridized microarray slide is scanned using microarray scanner.

Hybridization pattern: The microarray scan data is processed for data extraction using software, by which the information from probe features is extracted from microarray scan data to become probe-linked signal intensity. Including in this step is also background normalization, $\log_{in}$ transformation of signal intensity.

Mathematic equation: The simple linear regression analysis is performed based on the information of $\log_{10}$ (INTENSITY$_C$) and $\log_{10}$(CN$_C$). Y=0.6161+0.569× is a putative equation generated from the regression analysis of series of control signal intensities and copy numbers in FIG. 6; those are the signal intensities of SS-target 501 at spot 601/602/and so on and the SS-probe copy numbers at spot 601/602/and so on.

Determining the copy number of human miRNA sample of interest: The sample copy number is calculated by: $X=10^{(Y-0.6161)/0.569}$. Thus, when the putative normalized signal intensity of human miRNA Si located by the probe at spot 600*i* is 3, (3−0.6161)/0.569=4.18963; the copy number of human miRNA Si in 100 ng total RNA is: $X=10^{4.18963}=15475$ copies.

Figure 11:
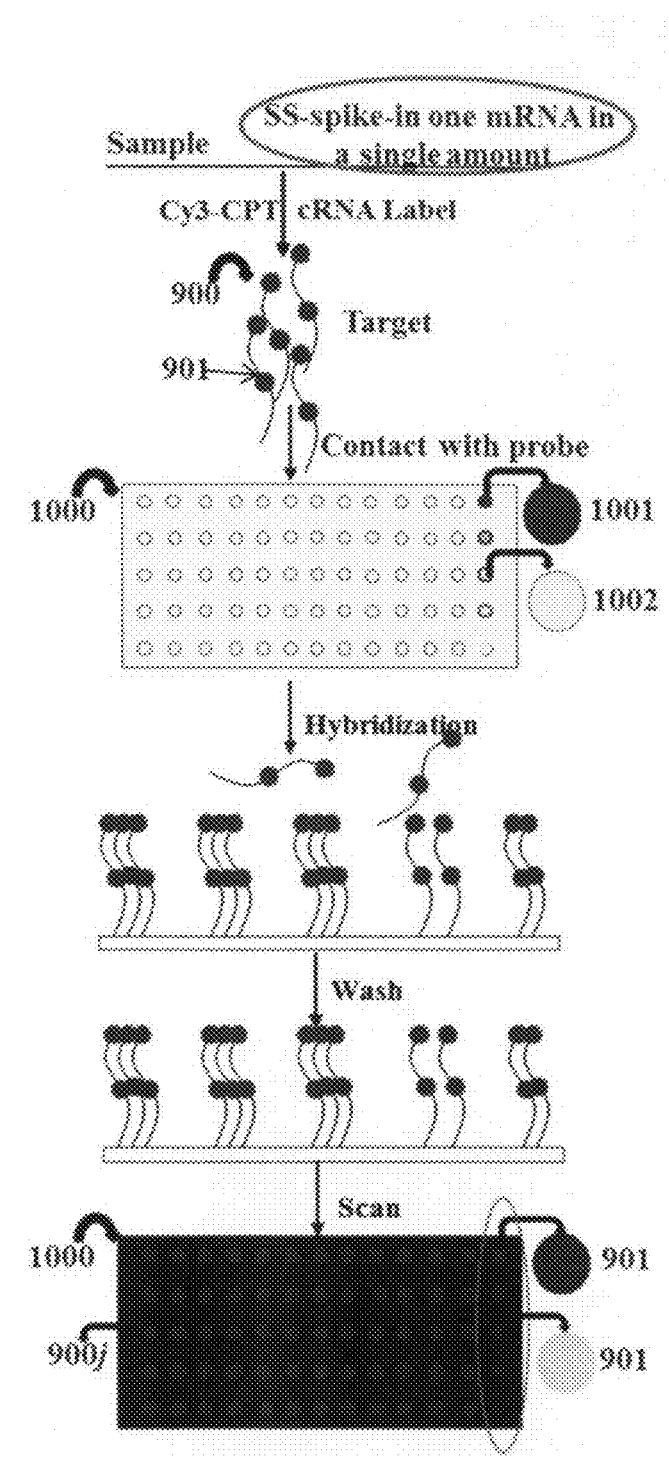
FIG. 11 provides a schematic representation of built-in standard curve with SS-spike-in method in multi-nucleotide labeling microarray technology (labeling method two).

2. Human gene expression microarray and FIG. 11 are employed to serve as an example to explain how built-in standard curve is used in the labeling method two to assay the mRNA copy number profile of the biological sample of interest.

Foreign mRNA chosen to engineer standard curve: The *arabidopsis thaliana* peroxisomal small heat shock protein Hsp15.7 mRNA (GenBank Accession: DQ403190) is employed to generate a built-in standard curve control on human gene expression microarray. This gene mRNA has 414 bp with 112 "G" residues. The plasmid DNA with the insert of DQ403190 from original ERC (LEMIRE et al. 2011) is cleaved into a single linear strand, and then in vitro transcription is performed using Ambion MEGAscript® T7 Kit to generate control mRNA (DEVONSHIRE et al. 2010). The mRNA obtained from the transcription is purified and quantitated to be ready as SS-target 901.

The probe of standard curve: A fragment sequence with 60 nucleotides of DQ403190 is selected as control probe, synthesized, purified and quantitated to be ready as SS-probe. The SS-probe is then printed on the standard 1"×3" microscope glass slide surface, which is activated to be able to immobilize the oligonucleotides, in triplicates with serial copy number dilutions (range from $10^3$ to $10^{10}$ copies) using SurePrint inkjet technology. The spot 1001 and 1002 are examples of SS-probe spots, along with printed spots of human mRNA probes on the same slide.

SS-spike-in: The *arabidopsis thaliana* peroxisomal small heat shock protein Hsp15.7 mRNA, defined as SS-target 901, is added to 1000ng total human RNA sample with the amount of 2× of SS-probe copy number that is printed on the glass slide, which is $2\times3\times(10^3+10^4+10^5+10^6+10^7+10^8+10^9+10^{10})$ copies.

Labeling: The total human RNA with SS-target 901 is subjected to 1$^{st}$ strand cDNA synthesis, and then the 1$^{st}$ strand cDNA is subjected to 2$^{nd}$ strand cDNA synthesis. The 2$^{nd}$ strand cDNA is used as template for in vitro transcription and labeling with cyanine 3-CTP, thus, the labeled transcript RNA is an antisense cRNA with labeled Cy3-C that has the equal number to "G" residues on the original mRNA, for example, labeled SS-target 901 has 112 Cy3-C residues.

Hybridization: The labeled cRNA is added into the chamber that is loaded with a microarray slide for hybridization.

Washing: The hybridized microarray slide is washed using washing buffer.

Scanning: The hybridized microarray slide is scanned using microarray scanner.

Hybridization pattern: The microarray scan data is processed for data extraction using software, by which the information from probe features is extracted from microarray scan data to become probe-linked signal intensity. Including in this step is also background normalization.

SIU transformation: Background normalized signal intensity is subjected to SIU transformation. For the SIU of SS-target at spot 1001, since the SS-target 901 has 112 labeled "C" residues, SIU$_{1001}$=INTENSITY$_{1001}$/112. Here is a critical transformation step; each gene has its specific transformation formula according to the gene sequence that can be obtained from GenBank. For example, human interleukin 2 (IL2) mRNA (GenBank Accession: NM_000586) has 822 bp nucleotides with 85 "G" residues and its probe is located at spot 900*j*, therefore, SIU$_{900j}$=ITENSITY$_{900j}$/85.

Logarithm transformation: SIU and CN are subjected $\log_{in}$ transformation.

Mathematic equation: The simple linear regression analysis is performed based on the information of $\log_{10}$ (SIU$_C$) and $\log_{10}$(CN$_C$). Y=0.6161+0.569× is a putative equation generated from the regression analysis of normalized series of signal intensities and copy numbers of SS-spike-in in FIG. 11, e.g., the signal intensities of SS-target 901 at spot 1001/1002/and so on and the SS-probe copy numbers at spot 1001/1002/and so on.

Determining the copy number of human mRNA sample of interest: The sample copy number is calculated by: $X=10^{(Y-0.6161)/0.569}$. Thus, when the putative normalized and $\log_{in}$ transformed SIU of human mRNA $5_{900j}$ located by the probe at spot 1000$j$ is 3, $(3-0.6161)/0.569=4.18963$; the copy number of human mRNA $5_{900j}$ in 1000ng total RNA is: $X=10^{4.18963}=15475$ copies.

3. RT-qPCR (reverse transcription qPCR) array and FIG. 7 are employed to serve as an example to explain how built-in standard curve is used in the labeling method three to assay the mRNA copy number profile of biological sample of interest.

mRNA sequence chosen to engineer standard curve: The human beta actin (ACTB) mRNA (GenBank Accession: NM_001101) is employed to generate a built-in standard curve for PCR array. This gene has 1852 bp mRNA. The cDNA of ACBT is generated through cloned plasmid amplification, and then the insert of the cDNA of NM_001101 is cleaved into a single linear strand, purified and quantitated to be ready as control template.

The control template of standard curve: The purified cDNA of ACBT is deposited into the wells of multiple-well plate 700 with serial copy number dilutions (range from $10^2$ to $10^8$ copies) in triplicate. The 701 and 702 are examples of control wells.

Reverse transcription: The human total RNA 50 ng of interest and mouse total RNA 50 ng of control are subjected to $1^{st}$ cDNA synthesis with oligo(dT) primers, respectively.

Figure 15:
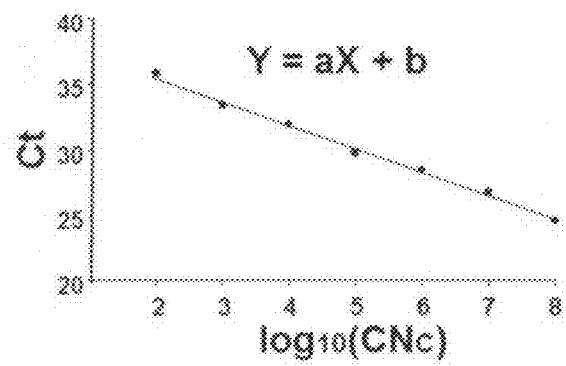
FIG. 15 provides a putative standard curve and linear regression equation of the prior art computational method of absolute PCR.

PCR amplification: The real-time PCR is performed using the standard method in the art with dsDNA dye SYBR Green I. RT of human RNA is added into sample wells; RT of mouse RNA is added into control/standard curve wells Traditional absolute estimation of the initial abundance of amplicon by standard curve is described in the following to help to illustrate the difference between the present invention and the prior art practice of absolute standard curve in real-time PCR: i). In the traditional practice, the control template for standard curve is the same sequence of the sample gene of interest, thus, each gene of interest needs one standard curve, which is cumbersome. ii). The serial dilution of standard curve is done individually for each experiment, thus, standardization is not practicable. iii). In the traditional practice, the linear regression of standard curve is based on the threshold cycle (Ct) and copy number, see a putative traditional linear regression in FIG. 15. (STRISSEL et al. 2012, JENKINS et al. 2005, Applied Biosystems).

In some embodiments of the present invention, the combined use of fluorescence intensities that can be optionally obtained from each PCR cycle (i.e., not just the one threshold cycle (Ct) of the whole PCR reaction) and the concept of IU to make separate standard curve for different PCR cycle can be optionally applied to: 1) reduce the need of number of standard curves, thus, one standard curve may be suitable for the copy number assay of many genes; 2) greatly increase the accuracy of gene copy number assay. Following steps are detail description of the present invention on mathematic calculations.

PCR product length: The forward and reverse primers of ACBT are chosen at 1045 for forward primer beginning and 1108 for reverse primer end, thus, the PCR product length of ACBT is 64 bp. Human angiotensin II receptor variant 1 gene (AT1, GenBank Accession: AY221090) is employed to be an example of sample gene of interest, and it has 1080 bp. The forward and reverse primers of AT1 are chosen at 434 for forward primer beginning and 501 for reverse primer end, thus, the PCR product length of AT1 is 68 bp.

Figure 16:
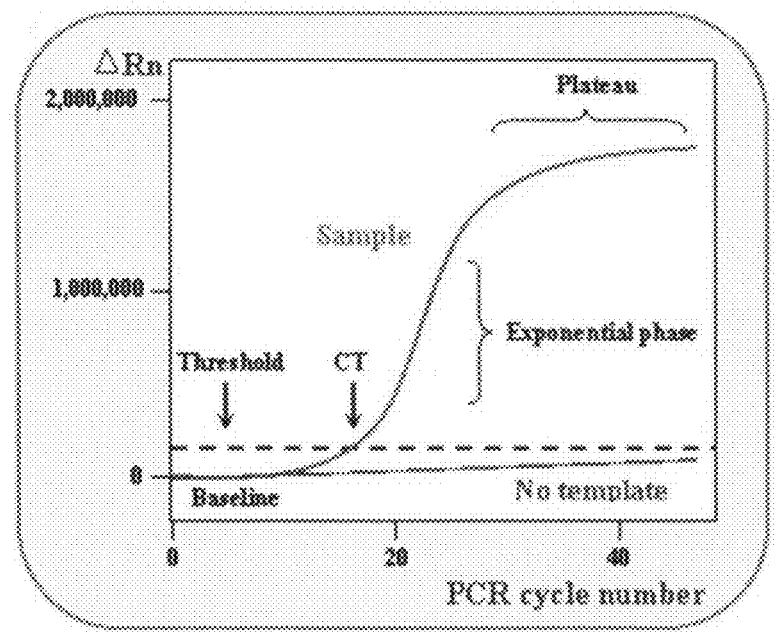
FIG. 16 illustrates threshold, exponential and plateau phases of real-time PCR amplification.

SIU calculation: Background normalized signal intensity is subjected to SIU transformation. Therefore, when the difference of fluorescence intensity between A-T and C-G is not concerned, the SIU of control ACBT at spot 701, $SIU_{701}=INTENSITY_{701}/64$; the SIU of sample AT1 at spot 700$k$, $SIU_{700k}=INTENSITY_{700k}/68$ (see FIG. 7). Here is a critical transformation step; each gene has its specific transformation formula according to the amplicon size based on the primer locations. This transformation is performed on all data between threshold and plateau cycles, which are the exponential phase (see FIG. 16).

Logarithm transformation: Both of SIU and CN are subjected to $\log_{in}$ transformation.

Mathematic equation: The simple linear regression analysis of each cycle is performed based on the information of $\log_{10}(SIU_C)$ and $\log_{10}(CN_C)$. $Y=0.6161+0.569\times$ is a putative equation of cycle 20, which is generated from the regression analysis of normalized series of signal intensities and copy numbers of ACBT in FIG. 7, e.g., the signal intensities of spot 701/702/and so on and template copy numbers at spot 701/702/and so on.

Determination of the copy number of human mRNA sample: The regression equation selected to back-calculation is decided by the Ct of sample of interest. For example, if the Ct of AT1 is 20, its copy number is calculated by: $X=10^{(Y-0.6161)/0.569}$. Thus, when the putative normalized signal intensity of human mRNA $S_{AT1}$ located by the primers at spot 700$k$ is 3 at cycle 20, $(3-0.6161)/0.569=4.18963$; the copy number of human mRNA AT1 in 50 ng total RNA is: $10^{4.18963}=15475$ copies.

REFERENCES

1. COLLINS, Has the revolution arrived?, Nature, 2010, pp. 674-5, vol. 464.
2. JURADO et al., Absolute gene expression patterns of thioredoxin and glutaredoxin redox systems in mouse, J Biol Chem, 2003, pp. 45546-54, vol. 278.
3. MIURA et al., Absolute quantification of the budding yeast transcriptome by means of competitive PCR between genomic and complementary DNAs, BMC Genomics, 2008, pp. 574, vol. 9.
4. STRISSEL et al., Reactivation of codogenic endogenous retroviral (ERV) envelope genes in human endometrial carcinoma and prestages: Emergence of new molecular targets, Oncotarget, 2012, pp. 1204-19, vol. 3.
5. SCHENA et al., Quantitative monitoring of gene expression patterns with a complementary DNA microarray, Science, 1995, pp. 467-70, vol. 270.
6. HANNAH et al., Global mRNA changes in microarray experiments, Nat Biotechnol, 2008, pp. 741-2, vol. 26.
7. MALONE et al., Microarrays, deep sequencing and the true measure of the transcriptome, BMC Biology, 2011, pp. 34, vol. 9.

8. SHENDURE et al., Next-generation DNA sequencing, Nat Biotech, 2008, pp. 1135-45, vol. 26.
9. FULLER et al., The challenges of sequencing by synthesis, Nat Biotech, 2009, pp. 1013-23, vol. 27.
10. METZKER, Sequencing technologies—the next generation, Nat Rev Genet, 2009, pp. 31-46, vol. 11.
11. MAHMOOD et al., Technique, Theory, and Trouble Shooting, N Am J Med Sci. September, 2012, pp. 429-434, vol. 4.
12. LEQUIN, Enzyme immunoassay (EIA)/enzyme-linked immunosorbent assay (ELISA), Clin Chem, 2005, pp. 2415-8, vol. 51.
13. TEMPLIN et al., Protein microarray technology, Trends Biotechnol, 2002, pp. 160-6, vol. 20.
14. CRETICH et al., Protein microarray technology: how far off is routine diagnostics?, Analyst, 2014, pp. 528-42, vol. 139.
15. TAO et al., Functional genomics: expression analysis of *Escherichia coli* growing on minimal and rich media, J Bacteriol, 1999, pp. 6425-40, vol. 181.
16. CARNEY et al. Functional genomics identifies neural stem cell sub-type expression profiles and genes regulating neuroblast homeostasis, Dev Biol, 2012, pp. 137-46, vol. 361.
17. RENAUD et al., trieFinder: an efficient program for annotating Digital Gene Expression (DGE) tags, BMC Bioinformatics, 2014, pp. 329, vol. 15.
18. BALL et al., Standards for microarray data, Science, 2002, pp. 539, vol. 298.
19. GERSHON, Microarray technology: an array of opportunities, Nature, 2002, pp. 885-91, vol. 416.
20. QUACKENBUSH, Genomics. Microarrays—guilt by association, Science, 2003, pp. 240-1, vol. 302.
21. BAMMLER et al., Standardizing global gene expression analysis between laboratories and across platforms, Nat Methods, 2005, pp. 351-6, vol. 2.
22. ALLISON et al., Microarray data analysis: from disarray to consolidation and consensus, Nat Rev Genet, 2006, pp. 55-65, vol. 7.
23. JONES et al., The Functional Genomics Experiment model (FuGE): an extensible framework for standards in functional genomics, Nat Biotechnol, 2007, pp. 1127-33, vol. 25.
24. IOANNIDIS et al., Repeatability of published microarray gene expression analyses. Nat Genet, 2009, pp. 149-55, vol. 41.
25. National Institutes of Health (NIH): Big Data to Knowledge (BD2K) Initiative (bd2k.nih.gov)
26. WARREN et al., Transcription factor profiling in individual hematopoietic progenitors by digital RT-PCR, Proc Natl Acad Sci USA, 2006, pp. 17807-12, vol. 103.
27. FU et al., Digital encoding of cellular mRNAs enabling precise and absolute gene expression measurement by single-molecule counting, Anal Chem, 2014, pp. 2867-70, vol. 86.
28. MOJTAHEDI et al., Direct elicitation of template concentration from quantification cycle (Cq) distributions in digital PCR, Nucleic Acids Res, 2014, pp. e126, vol. 42.
29. SANDERS et al., Evaluation of digital PCR for absolute DNA quantification, Anal. Chem., 2011, pp. 6474-84, vol. 83.
30. ADAMS et al., Complementary DNA sequencing: expressed sequence tags and human genome project, Science, 1991, pp. 1651-6, vol. 252.
31. VELCULESCU et al., Serial analysis of gene expression, Science, 1995, pp. 484-7, vol. 270.
32. REINARTZ et al., Massively parallel signature sequencing (MPSS) as a tool for in-depth quantitative gene expression profiling in all organisms, Brief Funct Genomic Proteomic, 2002, pp. 95-104, vol. 1.
33. BRENNER et al., Gene expression analysis by massively parallel signature sequencing (MPSS) on microbead arrays, Nat Biotechnol, 2000, pp. 630-4, vol. 18.
34. TORRES et al., Gene expression profiling by massively parallel sequencing, Genome Res, 2008, pp. 172-7, vol. 18.
35. RALLAPALLI et al., EXPRSS: an Illumine based high-throughput expression-profiling method to reveal transcriptional dynamics, BMC Genomics, 2014, pp. 341, vol. 15.
36. MORTAZAVI et al., Mapping and quantifying mammalian transcriptomes by RNA-Seq, Nat Methods, 2008, pp. 621-8, vol. 5.
37. LEE et al., Improving metabolic flux predictions using absolute gene expression data, BMC Syst Biol, 2012, pp. 73, vol. 6.
38. XU et al., CarrotDB: a genomic and transcriptomic database for carrot, Database (Oxford), 2014, pp. bau096, vol. 2014.
39. MUNGER et al., RNA-Seq Alignment to Individualized Genomes Improves Transcript Abundance Estimates in Multiparent Populations, Genetics, 2014, pp. 59-73, vol. 198.
40. GU et al., BADGE: A novel Bayesian model for accurate abundance quantification and differential analysis of RNA-Seq data, BMC Bioinformatics, 2014, pp. S6, vol. 15 Suppl 9.
41. RAPAPORT et al., Comprehensive evaluation of differential gene expression analysis methods for RNA-seq data, Genome Biol, 2013, pp. R95, vol. 14.
42. National Human Genome Research Institute (NHGRI): the Encyclopedia of DNA Elements (ENCODE) Consortium (www.genome.gov)
43. KELLIS et al., Defining functional DNA elements in the human genome, Proc Natl Acad Sci USA, 2014, pp. 6131-8, vol. 111.
44. DJEBALI et al., Landscape of transcription in human cells, Nature, 2012, pp. 101-8, vol. 489.
45. PACHTER, Estimating number of transcripts from RNA-Seq measurements, Bits of DNA: Reviews and Commentary on Computational Biology, 2014 (liorpachter.wordpress.com)
46. MARINOV et al., From single-cell to cell-pool transcriptomes: stochasticity in gene expression and RNA splicing, Genome Res, 2014, pp. 496-510, vol. 24.
47. ARMSTRONG, 6 Changes That'll Make a Big Difference With Your RNA-seq, Cofactor Genomics, 2014 (cofactorgenomics.com)
48. GIT et al., Systematic comparison of microarray profiling, real-time PCR, and next-generation sequencing technologies for measuring differential microRNA expression, RNA, 2010, pp. 991-1006, vol. 16.
49. CHAN et al., Conservation of core gene expression in vertebrate tissues, J Biol, 2009, pp. 33, vol. 8.
50. ARBEITMAN et al., Gene expression during the life cycle of *Drosophila melanogaster*, Science, 2002, pp. 2270-5, vol. 297.
51. SPELLMAN et al., Comprehensive identification of cell cycle-regulated genes of the yeast *Saccharomyces cerevisiae* by microarray hybridization, Mol Biol Cell, 1998, pp. 3273-97, vol. 9.

52. ALIZADEH et al., Distinct types of diffuse large B-cell lymphoma identified by gene expression profiling, Nature, 2000, pp. 503-11, vol. 403.
53. GOLUB et al., Molecular classification of cancer: class discovery and class prediction by gene expression monitoring, Science, 1999, pp. 531-7, vol. 286.
54. BREM et al., Genetic dissection of transcriptional regulation in budding yeast, Science, 2002, pp. 752-5, vol. 296.
55. ZHANG et al., Constraint and turnover in sex-biased gene expression in the genus *Drosophila*, Nature, 2007, pp. 233-7, vol. 450.
56. SHI et al., The MicroArray Quality Control (MAQC)-II study of common practices for the development and validation of microarray-based predictive models, Nat Biotechnol, 2010, pp. 827-38, vol. 28.
57. ADABOR et al., SAGA: A hybrid search algorithm for Bayesian Network structure learning of transcriptional regulatory networks, J Biomed Inform, 2015, pp. 27-35, vol. 53.
58. KORUCUOGLU et al., Bayesian pathway analysis of cancer microarray data, PLoS One, 2014, pp. e102803, vol. 9.
59. EISEN et al., DNA arrays for analysis of gene expression, Methods Enzymol, 1999, pp. 179-205, vol. 303.
60. EISEN et al., Cluster analysis and display of genome-wide expression patterns, Proc Natl Acad Sci USA, 1998, pp. 14863-8, vol. 95.
61. ROSS et al., Systematic variation in gene expression patterns in human cancer cell lines, Nat Genet, 2000, pp. 227-35, vol. 24.
62. CHANG et al., Diversity, topographic differentiation, and positional memory in human fibroblasts, Proc Natl Acad Sci USA, 2002, pp. 12877-82, vol. 99.
63. PEROU et al., Molecular portraits of human breast tumours, Nature, 2000, pp. 747-52, vol. 406.
64. GARBER et al., Diversity of gene expression in adenocarcinoma of the lung, Proc Natl Acad Sci USA, 2001, pp. 13784-9, vol. 98.
65. CHEN et al., Gene expression patterns in human liver cancers, Mol Biol Cell, 2002, pp. 1929-39, vol. 13.
66. WHITFIELD et al., Identification of genes periodically expressed in the human cell cycle and their expression in tumors, Mol Biol Cell, 2002, pp. 1977-2000, vol. 13.
67. PUSKAS et al., Production of bulk amounts of universal RNA for microarrays, Biotechniques, 2002, pp. 898-900, vol. 33.
68. STERRENBURG et al., A common reference for cDNA microarray hybridizations, Nucleic Acids Res, 2002, pp. e116, vol. 30.
69. WEIL et al., Toward a universal standard: comparing two methods for standardizing spotted microarray data, Biotechniques, 2002, pp. 1310-4, vol. 32.
70. NOVORADOVSKAYA et al., Pooled, high-quality Reference RNA for human microarrays, Strategies, 2000, pp. 121-2, vol. 13.
71. LOCKHART et al., Expression monitoring by hybridization to high-density oligonucleotide arrays, Nat Biotechnol, 1996, pp. 1675-80, vol. 14.
72. SARTOR et al., Intensity-based hierarchical Bayes method improves testing for differentially expressed genes in microarray experiments, BMC Bioinformatics, 2006, pp. 538, vol. 7.
73. ZHOU et al., MicroRNA profiling using microParaflo microfluidic array technology, Methods Mol Biol, 2012, pp. 153-82, vol. 822.
74. HILL et al., Evaluation of normalization procedures for oligonucleotide array data based on spiked cRNA controls, Genome Biol, 2001, pp. research0055, vol. 2.
75. CHOE et al., Preferred analysis methods for Affymetrix GeneChips revealed by a wholly defined control dataset, Genome Biol, 2005, pp. R16, vol. 6.
76. COPE et al., A benchmark for Affymetrix GeneChip expression measures, Bioinformatics, 2004, pp. 323-31, vol. 20.
77. WELSH et al., Iterative rank-order normalization of gene expression microarray data, BMC Bioinformatics, 2013, pp. 153, vol. 14.
78. WOFINGER et al., Assessing gene significance from cDNA microarray expression data via mixed models, Journal of Computational Biology, 2001, pp. 625-37, vol. 8.
79. CHU et al., A systematic statistical linear modeling approach to oligonucleotide array experiments, Mathematical Biosciences, 2002, pp. 35-51, vol. 176.
80. YANG et al., Design and analysis of comparative microarray experiments, Statistical Analysis of Gene Expression Microarray Data, 2003, pp. 35-91, Taylor & Francis.
81. FRIEDMAN et al., Using Bayesian networks to analyze expression data, J Comput Biol, 2000, pp. 601-20, vol. 7.
82. BALDI et al., A Bayesian framework for the analysis of microarray expression data: regularized t-test and statistical inferences of gene changes, Bioinformatics, 2001, pp. 509-19, vol. 17.
83. LONG et al., Improved statistical inference from DNA microarray data using analysis of variance and a Bayesian statistical framework. Analysis of global gene expression in *Escherichia coli* K12, J Biol Chem, 2001, pp. 19937-44, vol. 276.
84. TOWNSEND et al., Bayesian analysis of gene expression levels: statistical quantification of relative mRNA level across multiple strains or treatments, Genome Biol, 2002, pp. research 0071, vol. 3.
85. SMYTH, Linear models and empirical bayes methods for assessing differential expression in microarray experiments, Stat Appl Genet Mol Biol, 2004, pp. Article 3, vol. 3.
86. NEWTON et al., On differential variability of expression ratios: improving statistical inference about gene expression changes from microarray data, J Comput Biol, 2001, pp. 37-52, vol. 8.
87. LIANG et al., Hierarchical Bayesian neural network for gene expression temporal patterns, Stat Appl Genet Mol Biol, 2004, pp. Article20, vol. 3.
88. SEITA et al., Gene Expression Commons: an open platform for absolute gene expression profiling, PLoS One, 2012, pp. e40321, vol. 7.
89. FRIGESSI et al., Genome-wide estimation of transcript concentrations from spotted cDNA microarray data, Nucleic Acids Res, 2005, pp. e143, vol. 33.
90. NYGAARD et al., Limitations of mRNA amplification from small-size cell samples, BMC Genomics, 2005, pp. 147, vol. 6.
91. NYGAARD et al., Validation of oligoarrays for quantitative exploration of the transcriptome, BMC Genomics, 2008, pp. 258, vol. 9.
92. HELD et al., Relationship between gene expression and observed intensities in DNA microarrays—a modeling study, Nucleic Acids Res, 2006, pp. e70, vol. 34.
93. CALZA et al., Normalization of oligonucleotide arrays based on the least-variant set of genes, BMC Bioinforma, 2008, pp. 140, vol. 9.

94. NISHIYAMA et al., Systematic repression of transcription factors reveals limited patterns of gene expression changes in ES cells, Sci Rep, 2013, pp. 1390, vol. 3.
95. HIRATA et al., Zscan4 transiently reactivates early embryonic genes during the generation of induced pluripotent stem cells, Sci Rep, 2012, pp. 208, vol. 2.
96. YANG et al., Within the fold: assessing differential expression measures and reproducibility in microarray assays, Genome Biol, 2002, pp. research0062, vol. 3.
97. NOVORADOVSKAYA et al. Universal Reference RNA as a standard for microarray experiments, BMC Genomics, 2004, pp. 20, vol. 5.
98. BISSELS et al., Absolute quantification of microRNAs by using a universal reference, RNA, 2009, pp. 2375-84, vol. 15.
99. SHI et al., The MicroArray Quality Control (MAQC)-II study of common practices for the development and validation of microarray-based predictive models, Nat Biotechnol, 2010, pp. 827-38, vol. 28.
100. DUDLEY et al., Measuring absolute expression with microarrays with a calibrated reference sample and an extended signal intensity range, Proc Natl Acad Sci USA, 2002, pp. 7554-9, vol. 99.
101. CARTER et al., Transcript copy number estimation using a mouse whole-genome oligonucleotide microarray, Genome Biol, 2005, pp. R61, vol. 6.
102. TURNER et al., Biosensors: Fundamentals and Applications, 1987, pp. 770, Oxford University Press, UK.
103. BĂNICĂ, Chemical Sensors and Biosensors:Fundamentals and Applications, 2012, pp. 576, John Wiley & Sons, UK.
104. SIN et al., Advances and challenges in biosensor-based diagnosis of infectious diseases, Expert Rev Mol Diagn, 2014, pp. 225-44, vol. 14.
105. ESTEVEZ et al., Trends and challenges of refractometric nanoplasmonic biosensors: a review, Anal Chim Acta, 2014, pp. 55-73, vol. 806.
106. BAKER, MicroRNA profiling: separating signal from noise, Nat Methods, 2010, pp. 687-92, vol. 7.
107. LESHKOWITZ et al., Differences in microRNA detection levels are technology and sequence dependent, RNA, 2013, pp. 527-38, vol. 19.
108. RYDEN et al., Evaluation of microarray data normalization procedures using spike-in experiments, BMC Bioinformatics, 2006, pp. 300, vol. 7.
109. BENES et al., Standardization of protocols in cDNA microarray analysis, Trends Biochem Sci, 2003, pp. 244-9, vol. 28.
110. FARDIN et al., Normalization of low-density microarray using external spike-in controls: analysis of macrophage cell lines expression profile, BMC Genomics, 2007, pp. 17, vol. 8.
111. LEMIRE et al., Development of ERCC RNA Spike-In Control Mixes, J Biomol Tech, 2011, pp. S46, vol. 22(Suppl).
112. YAUK et al., Novel design and controls for focused DNA microarrays: applications in quality assurance/control and normalization for the Health Canada ToxArray, BMC Genomics, 2006, pp. 266, vol. 7.
113. ALVO et al., Testing for mean and correlation changes in microarray experiments: an application for pathway analysis, BMC Bioinformatics, 2010, pp. 60, vol. 11.
114. MALIK et al., Hepatic mRNA, microRNA, and miR-34a-target responses in mice after 28 days exposure to doses of benzo(a)pyrene that elicit DNA damage and mutation, Environ Mol Mutagen, 2012, pp. 10-21, vol. 53.
115. MACKAY et al., Real-time PCR in virology, Nucleic Acids Res, 2002, pp. 1292-305, vol. 30.
116. BioSearch Technologies: Dyes & Fluorescence detection chemistry in qPCR (www.biosearchtech.com)
117. BENGTSSON et al., A new minor groove binding asymmetric cyanine reporter dye for real-time PCR, Nucleic Acids Res, 2003, pp. e45, vol. 31.
118. WITTWER et al., Continuous fluorescence monitoring of rapid cycle DNA amplification, Biotechniques, 1997, pp. 130-1, 134-8, vol. 22.
119. National Center for Biotechnology Information (NCBI) Probe Database: TaqMan® Gene Expression (www.ncbi.nlm.nih.gov).
120. HOLLAND et al., Detection of specific polymerase chain reaction product by utilizing the 5'----3' exonuclease activity of *Thermus aquaticus* DNA polymerase, Proc Natl Acad Sci USA, 1991, pp. 7276-80, vol. 88.
121. RICH et al., Higher-throughput, label-free, real-time molecular interaction analysis, Analytical biochemistry, 2007, pp. 1-6, vol. 361.
122. LIEDBERG et al., Surface plasmon resonance for gas detection and biosensing, Sensors and Actuators, 1983, pp. 299-304, vol. 4.
123. O'MALLEY et al., Label-free high-throughput functional lytic assays, J Biomol Screen, 2007, pp. 117-25, vol. 12.
124. WEMMER, Structure and dynamics by NMR, Nucleic Acids: Structures, Properties, and Functions, 2000, pp. 111, University Science Books, California.
125. BROOKS et al., High-throughput epitope binning of therapeutic monoclonal antibodies: why you need to bin the fridge, Drug Discov Today, 2014, pp. 1040-4, vol. 19.
126. CHEN et al., Visualization of high-throughput and label-free antibody-polypeptide binding for drug screening based on microarrays and surface plasmon resonance imaging, J Biomed Opt, 2012, pp. 015005, vol. 17.
127. Lautner et al., Monitoring of interactions between aptamers and human IgE by Surface Plasmon Resonance imaging, HORIBA Scientific Application Note (www.horiba.com).
128. DEVONSHIRE et al., Evaluation of external RNA controls for the standardisation of gene expression biomarker measurements, BMC Genomics, 2010, pp. 662, vol. 11.
129. JENKINS et al., Differential expression of IGF-binding protein-3 in normal and malignant colon and its influence on apoptosis, Endocr Relat Cancer, 2005, pp. 891-901, vol. 12.
130. Applied Biosystems 7300/7500/7500 Fast Real-Time PCR System: Absolute Quantitation Using Standard Curve Getting Started Guide (www.appliedbiosystems.com).

What is claimed is:

1. A method of determining absolute quantity of at least one sample target, comprising:
   i) providing a solid support having a series of control partner 1 and one of at least one sample probe and at least one sample target attached thereon, wherein the series of control partner 1 and the one of the at least one sample probe and the at least one sample target are at separate locations of the solid support, and each of the series of control partner 1 has a different and known copy number;
   ii) contacting the solid support with at least one control partner 2 and another of the at least one sample target and the at least one sample probe, wherein:

the series of control partner 1 are configured to recognize and bind the at least one control partner 2, resulting directly or indirectly in a series of detectable control signals, wherein an intensity of each detectable control signal correlates with the known copy number of the each of the series of control partner 1, and a copy number of each of the at least one control partner 2 is no less than the known copy number of the each of the series of control partner 1; and the at least one sample probe is configured to recognize and bind the at least one sample target in a corresponding manner, resulting directly or indirectly in at least one detectable sample signal, wherein an intensity of each detectable sample signal correlates with a copy number of each of the at least one sample target, and a copy number of each of the at least one sample probe is no less than the copy number of the each of the at least one sample target;

iii) detecting the series of detectable control signals and the at least one detectable sample signal;

iv) making a standard curve relating the intensity of each of the series of detectable control signals with the known copy number of the each of the series of control partner 1; and v) determining the copy number of each of the at least one sample target by using the standard curve to translate the intensity of the each of the at least one detectable sample signal to the copy number of the each of the at least one sample target.

2. The method of claim 1, wherein each of the at least one control partner 2 is directly or indirectly labeled with one or more first basic labeling units, and the another of the at least one sample target and the at least one sample probe is directly or indirectly labeled with one or more second basic labeling units, wherein the series of detectable control signals and the at least one detectable sample signal derive from the first basic labeling units and the second basic labeling units respectively.

3. The method of claim 2, wherein the intensity of each detectable control signal is standardized by dividing with a number of the first basic labeling units per molecule of the each of the at least one control partner 2, and the intensity of each detectable sample signal is standardized by dividing with a number of the second basic labeling units per molecule of the another of the at least one sample target and the at least one sample probe.

4. The method of claim 2, wherein at least one of labeling of the at least one control partner 2 with the one or more first basic labeling units and labeling of the another of the at least one sample target and the at least one sample probe with the one or more second basic labeling units is realized by a labeling method by applying from the group consisting of: (i) fluorophore, (ii) chemiluminescent agent, (iii) silver, (iv) affinity, (v) photochemical agent, (vi) enzyme, (vii) chromophore, and (viii) radioisotope tag.

5. The method of claim 2, wherein the first basic labeling unit and the second basic labeling unit are identical.

6. The method of claim 1, wherein the series of control partner 1, the at least one control partner 2, the at least one sample target and the at least one sample probe are selected from the group consisting of: (i) DNA, (ii) RNA, (iii) protein, (iv) peptide, (v) polysaccharide, (vi) chemical compound and (vii) antibody.

7. The method of claim 1, wherein the solid support is selected from a group consisting of: (i) glass, (ii) plastic, (iii) silicon, (iv) microscopic polystyrene beads, (v) nitrocellulose membrane, (vi) PVDF, (vii) metal, (viii) multiple-well plate.

8. The method of claim 1, wherein step i) comprises:
providing the series of control partner 1 and the one of the at least one sample probe and the at least one sample target; and
attaching the series of control partner 1 and the one of the at least one sample probe and the at least one sample target onto the solid support.

9. The method of claim 1, wherein step i) comprises:
directly synthesizing the series of control partner 1 onto the solid support.

10. The method of claim 1, wherein the series of detectable control signals and the at least one detectable sample signal are detected with a microarray laser scanner, a plate reader, or a Western blot scanner.

11. The method of claim 1, wherein the series of detectable control signals and the at least one detectable sample signal are detected by a label-free technology.

12. The method of claim 11, wherein the label-free technology is surface plasmon resonance (SPR), microelectromechanical system (MEMS), carbon nanowire sensors, or carbon nanotubes.

13. The method of claim 1, wherein at least one of step iv) making a standard curve relating the intensity of each of the series of detectable control signals with the known copy number of the each of the series of control partner 1 and step v) determining the copy number of each of the at least one sample target by using the standard curve to translate the intensity of the each of the at least one detectable sample signal to the copy number of the each of the at least one sample target is carried out by a computer software.

* * * * *